United States Patent [19]

Fischer et al.

[11] Patent Number: 4,855,297
[45] Date of Patent: Aug. 8, 1989

[54] TRICYCLIC PYRIDONE DERIVATIVES

[75] Inventors: Ulf Fischer, Frenkendorf; Fernand Schneider, Basel; Widmer Ulrich, Rheinfelden, all of Switzerland

[73] Assignee: Hoffman-La Roche Inc., Nutley, N.J.

[21] Appl. No.: 937,934

[22] Filed: Dec. 4, 1986

[30] Foreign Application Priority Data

Dec. 13, 1985 [CH] Switzerland .................. 5324/85
Oct. 1, 1986 [CH] Switzerland .................. 3922/86

[51] Int. Cl.[4] .................. A61k 31/495; C07D 237/26
[52] U.S. Cl. .................. 514/248; 514/233.2; 514/227.8; 544/60; 544/115; 544/234
[58] Field of Search .................. 544/234, 3, 54, 58.6, 544/63, 96, 115, 60; 514/248, 183, 218, 222.2, 226.8, 227.8, 228.8, 233.2, 210, 211, 212; 540/1, 202, 355, 362, 599, 544, 575, 553

[56] References Cited

U.S. PATENT DOCUMENTS 4,735,940  4/1988  Fischer et al. .................. 514/212

Primary Examiner—Mary C. Lee
Assistant Examiner—E. Brendan Magrah

Attorney, Agent, or Firm—Jon S. Saxe; Bernard S. Leon; William G. Isgro

[57] ABSTRACT

The compounds of the formula

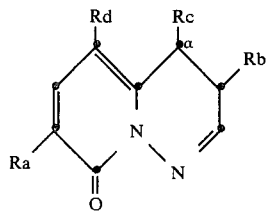

wherein $R_a, R_b, R_c, R_d$ are defined in the specification and pharmaceutically acceptable addition salts are disclosed.

The compounds of formula I have valuable pharmacological properties and can be used for the control of prevention of illnesses. In particular, they have muscle relevant, seditive-hypnotic, anxiolytic and/or anticonvulsive activity and can accordingly be used in the control or prevention of muscle tensions, stress conditions, isomnia, anxiety states and/or convulsions.

50 Claims, No Drawings

TRICYCLIC PYRIDONE DERIVATIVES

BRIEF SUMMARY OF THE INVENTION

The invention relates to compounds of the formula

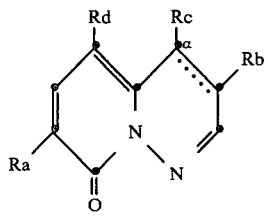

wherein Ra is a phenyl, pyridyl or thienyl group optionally substituted by halogen, trifluoromethyl, nitro, lower alkyl or lower alkoxy, Rb and Rc taken together with the carbon atom denoted by a α are a group of the formula $>C_\alpha-S-CH=CH-$ (a), $>C_\alpha-CH=CH-S-$ (b) or $>C_\alpha-CH=CH-CH=CH-$ (c) which is optionally substituted by halogen, trifluoromethyl, lower alkyl, lower alkoxy, nitro, amino or mono- or di(lower alkyl)amino and the dotted line is an additional bond, Rd is the group of the formula $-(A^1)_m-(CO)_n-(Q^1A^2)_q-R^1$, m, n and q each are the integer 0 or 1, $A^1$ is lower alkylene, $A^2$ is lower alkylene, a direct bond or the group $-CO-$, $Q^1$ is an oxygen atom or the group $-NR^2-$, $R^1$ is hydrogen, hydroxy, cyano, nitro, halogen, lower alkoxy, lower alkyl, lower alkoxycarbonyl, aryl, a group of the formula $-NR^3R^4$ or a 5-membered saturated, partially unsaturated or aromatic heterocycle which is attached via a carbon atom and which is optionally substituted by one or two lower alkyl groups and optionally substituted by a $(C_{3-6})$-cycloalkyl, hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or alkylenedioxy group, $R^2$ is hydrogen, lower alkyl or aryl, $R^3$ and $R^4$ each, independently, are hydrogen, lower alkyl, lower alkoxyalkyl, lower dialkoxyalkyl, lower alkylenedioxyalkyl, lower cyanoalkyl, lower haloalkyl, lower hydroxyalkyl, lower dihydroxyalkyl, lower alkanoyl, lower alkoxycarbonyl or a $(C_{3-7})$-cycloalkyl group which is optionally substituted by hydroxy, lower alkoxy, lower alkanoyloxy, lower hydroxyalkyl, lower alkoxyalkyl, lower alkanoyloxyalkyl, oxo, carbamoyl, mono- or di(lower alkyl)carbamoyl or by lower alkylenedioxy or $R^3$ and $R^4$ taken together with the nitrogen atom are a 3- to 7-membered saturated N-heterocycle which is optionally substituted by one or two lower alkyl groups and optionally substituted by one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or lower alkylenedioxy groups and which can contain as a ring member an oxygen or sulfur atom or the group $>N-R^5$, and $R^5$ is hydrogen, lower alkyl, lower hydroxyalkyl, lower alkoxyalkyl, lower alkanoyloxyalkyl, lower alkanoyl, lower alkoxycarbonyl, carbamoyl or mono- or di(lower alkyl)carbamoyl, with the proviso that n is the integer 0 when q is the integer 1 and $A^2$ is the group $-CO-$, that $R^1$ is other than cyano, nitro, halogen or lower alkoxycarbonyl when q is the number 0 and n is the number 1 or when q is the integer 1 and $A^2$ is the group $-CO-$, and that $R^1$ is other than hydroxy, cyano, nitro, halogen, lower alkoxycarbonyl, lower alkoxy and $-NR^3R^4$ when q is the integer 1 and $A^2$ is a direct bond, and pharmaceutically acceptable acid addition salts of compounds of formula I which have one or more basic substituents.

DETAILED DESCRIPTION OF THE INVENTION

The invention relates to compounds of the formula

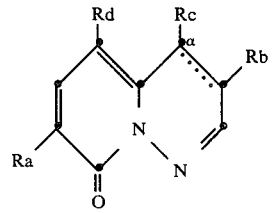

wherein Ra is a phenyl, pyridyl or thienyl group optionally substituted by halogen, trifluoromethyl, nitro, lower alkyl or lower alkoxy, Rb and Rc taken together with the carbon atom denoted by α are a group of the formula $>C_\alpha-S-CH=CH-$ (a), $>C_\alpha-CH=CH-S-$ (b) or $>C_\alpha-CH=CH-CH=CH-$ (c) which is optionally substituted by halogen, trifluoromethyl, lower alkyl, lower alkoxy, nitro, amino or mono- or di(lower alkyl)amino and the dotted line is an additional bond, Rd is the group of the formula $-(A^1)_m-(CO)_n-(Q^1A^2)_q-R^1$, m, n and q each are the integer 0 or 1, $A^1$ is lower alkylene, $A^2$ is lower alkylene, a direct bond or the group $-CO-$, $Q^1$ is an oxygen atom or the group $-NR^2-$, $R^1$ is hydrogen, hydroxy, cyano, nitro, halogen, lower alkoxy, lower alkyl, lower alkoxycarbonyl, aryl, a group of the formula $-NR^3R^4$ or a 5-membered saturated, partially unsaturated or aromatic heterocycle which is attached via a carbon atom and which is optionally substituted by one or two lower alkyl groups and optionally substituted by a $(C_{3-6})$-cycloalkyl, hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or alkylenedioxy group, $R^2$ is hydrogen, lower alkyl or aryl, $R^3$ and $R^4$ each, independently, are hydrogen, lower alkyl, lower alkoxyalkyl, lower dialkoxyalkyl, lower alkylenedioxyalkyl, lower cyanoalkyl, lower haloalkyl, lower hydroxyalkyl, lower dihydroxyalkyl, lower alkanoyl, lower alkoxycarbonyl or a $(C_{3-7})$-cycloalkyl group which is optionally substituted by hydroxy, lower alkoxy, lower alkanoyloxy, lower hydroxyalkyl, lower alkoxyalkyl, lower alkanoyloxyalkyl, oxo, carbamoyl, mono- or di(lower alkyl)carbamoyl or by lower alkylenedioxy or $R^3$ and $R^4$ taken together with the nitrogen atom are a 3- to 7-membered saturated N-heterocycle which is optionally substituted by one or two lower alkyl groups and optionally substituted by one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or lower alkylenedioxy groups and which can contain as a ring member an oxygen or sulfur atom or the group $>N-R^5$, and $R^5$ is hydrogen, lower alkyl, lower hydroxyalkyl, lower alkoxyalkyl, lower alkanoyloxyalkyl, lower alkanoyl, lower alkoxycarbonyl, carbamoyl or mono- or di(lower alkyl)carbamoyl, with the proviso that n is the integer 0 when q is the integer 1 and $A^2$ is the group —CO—, that $R^1$ is other than cyano, nitro, halogen or lower alkoxycarbonyl when q is the number 0 and n is the number 1 or when q is the integer 1 and $A^2$ is the group —CO—, and that $R^1$ is other than hydroxy, cyano, nitro, halogen, lower alkoxycarbonyl, lower alkoxy and —$NR^3R^4$ when q is the integer 1 and $A^2$ is a direct bond, and pharmaceutically acceptable acid addition salts of compounds of formula I which have one or more basic substituents.

The tricyclic pyridone derivatives have valuable pharmacological properties and can be used for the control or prevention of illnesses. In particular, they have muscle relaxant, sedative-hypnotic, anxiolytic and/or anticonvulsive activity and can accordingly be used in the control or prevention of muscle tensions, stress conditions, insomnia, anxiety states and/or convulsions.

Objects of the present invention are the compounds of formula I and their salts, a process and intermediates for their preparation, the preparation of the intermediates and their use for the preparation of therapeutically active substances, the compounds of formula I and their salts for use as therapeutically active substances, medicaments based on the compounds of formula I and their preparation, the use of the compounds of formula I in the control or prevention of illnesses, as well as their use for the preparation of medicaments having muscle relaxant, sedative-hypnotic, anxiolytic and/or anticonvulsive activity.

The term "lower" denotes residues and compounds having a maximum of seven, preferably a maximum of four, carbon atoms. The term "alkyl", taken alone or in combinations such as alkanoyl, alkanoyloxy and alkoxyalkyl, denotes straight-chain or branched, saturated hydrocarbon residues, such as, methyl, ethyl, propyl, isopropyl, t-butyl and the like. The term "cycloalkyl" denotes cyclic, saturated hydrocarbon residues of 3 to 7 carbon atoms such as cyclohexyl. The term "alkoxy" denotes alkyl groups attached via an oxygen atom, such as methoxy and ethoxy. The term "hydroxyalkyl" denotes alkyl groups substituted by hydroxy, such as 2-hydroxyethyl. The terms "alkanoyl" and "alkanoyloxy" denote fatty acid residues such as acetyl and acetoxy. The term "alkylene" denotes straight-chain or branched, saturated hydrocarbon residues having two free valencies, such as methylene, 1,2-ethylene and 1,3-propylene. The term "halogen" denotes the four forms fluorine, chlorine, bromine and iodine.

The term "aryl" preferably denotes phenyl groups which are optionally substituted by halogen, trifluoromethyl, lower alkyl, lower alkoxy, nitro, amino or mono- or di(lower alkyl)amino.

The 5-membered, saturated, partially unsaturated or aromatic heterocycles which are attached via a carbon atom preferably contain as the hetero ring member(s) an oxygen or sulfur atom or an imino or lower alkylamino group and optionally one or two nitrogen atoms, with the carbon atom via which the heterocycle is attached being preferably situated adjacent to one hetero atom or between two hetero atoms. Examples of such heterocycles, which can be substituted as mentioned earlier, are: 2-oxazolin-2-yl, 3-methyl-1,2,4-oxadiazol-5-yl, 3-cyclopropyl-1,2,4-oxadiazol-5-yl, 2-thiazolin-2-yl, 2-tetrahydrofuryl and 2-thiazolyl.

The term "3- to 7-membered, saturated N-heterocycle which can contain as a ring member an oxygen or sulfur atom or the group $>N-R^5$" as a possible value for —$NR^3R^4$ denotes on the one hand heterocycles having only one hetero atom, namely, the nitrogen atom via which they are attached, and on the other hand heterocycles having two hetero atoms, namely, the aforementioned nitrogen atom and an oxygen or sulfur atom or a second nitrogen atom. Examples of such heterocycles, which can be substituted as mentioned earlier, are: 2-(lower alkoxyalkyl)-1-azetidinyl, 3-(lower alkoxy)-1-azetidinyl, 3-hydroxy-1-azetidinyl, 2-(lower hydroxyalkyl)-1-azetidinyl, 2-(lower alkanoyloxyalkyl)-1-pyrrolidinyl, 3-oxo-1-pyrrolidinyl, 2-(lower alkoxycarbonyl)-1-pyrrolidinyl, 3-(lower alkoxy)-1-pyrrolidinyl, 3-hydroxy-1-pyrrolidinyl, 2-(lower alkoxyalkyl)-1-pyrrolidinyl, 2-(lower hydroxyalkyl)-1-pyrrolidinyl, 2-(lower hydroxyalkyl)-4-hydroxy-1-pyrrolidinyl, 2-(lower alkoxyalkyl)-4-(lower alkoxy)-1-pyrrolidinyl, 4-morpholinyl, 2,6-di-(lower alkyl)-4-morpholinyl, 4-thiomorpholinyl, 1-piperazinyl, 1-(lower alkyl)-4-piperazinyl, 1-(lower alkoxyalkyl)-4-piperazinyl, 1-(lower alkanoyl)-4-piperazinyl, 4-(lower hydroxyalkyl)-1-piperidinyl, 4-oxo-1-piperidinyl, 4-(lower alkoxy)-1-piperidinyl, 4-(lower alkoxycarbonyl)-1-piperidinyl, 4-hydroxy-1-piperidinyl, 4-(lower alkylcarbamoyl)-1-piperidinyl, 4-(lower alkanoyloxy)-1-piperidinyl, 2-(lower alkoxyalkyl)-1-piperidinyl, 2-(lower hydroxyalkyl)-1-piperidinyl, 3-(lower alkoxy)-1-piperidinyl, 4,4-(lower alkylenedioxy)-1-piperidinyl and 3-hydroxy-1-piperidinyl.

The symbol Ra preferably is a phenyl group optionally substituted by m-halogen or m-trifluoromethyl, with phenyl being especially preferred.

The symbols Rb and Rc together with the carbon atom denoted by α preferably is a group of the formula $>C_\alpha—S—CH=CH—$ (a) or $>C_\alpha—CH=CH—CH=CH—$ (c), which is optionally substituted by halogen, especially the group of the formula $>C_\alpha—S—CH=CH—$ or $>C_\alpha—CH=CCl—CH=CH—$, whereby the dotted line is an additional bond.

In a preferred embodiment, $Q^1$ is an oxygen atom, $A^2$ is the group —CO—, $R^1$ is the group —$NR^3R^4$, $R^3$ is lower alkyl or lower alkoxyalkyl and $R^4$ is hydrogen or lower alkyl or $R^3$ and $R^4$ together with the nitrogen atom is a 4-, 5- or 6-membered saturated N-heterocycle which is optionally substituted by one or two lower alkyl groups and optionally substituted by a hydroxy, lower alkoxy, lower hydroxyalkyl or lower alkoxyalkyl group and which can contain as a ring member an oxygen atom, and eith m and q is the integer 0 and n is the integer 1 or m and q is the integer 1 and n is the integer 0.

In an especially preferred embodiment, $A^1$ is methylene, $Q^1$ is an oxygen atom, $A^2$ is the group —CO—, $R^1$ is the group —$NR^3R^4$, $R^3$ is lower alkyl or lower alkoxyalkyl and $R^4$ is hydrogen or lower alkyl or $R^3$ and $R^4$ together with the nitrogen atom are a 1-azetidinyl, 1-pyrrolidinyl, 1-piperidinyl or 4-morpholinyl group which is optionally substituted by one or two lower alkyl groups and optionally substituted by a hydroxy, lower alkoxy, lower hydroxyalkyl or lower alkoxyalkyl group and either m and q is the integer 0 and n is the integer 1 or m and q is the integer 1 and n is the integer 0. In a particularly preferred embodiment, $A^1$ is methylene, $Q^1$ is an oxygen atom, $A^2$ is the group —CO—, $R^1$ is the group —$NR^3R^4$, $R^3$ is lower alkyl or 2-(lower alkoxy)ethyl and $R^4$ is hydrogen or lower alkyl or $R^3$ and $R^4$ together with the nitrogen atom are 3-(lower alkoxy)-1-azetidinyl, 3-(lower alkoxy)-1-pyrrolidinyl, 2-(lower alkoxyalkyl)-1-pyrrolidinyl, 2-(lower hydroxyalkyl)-1-pyrrolidinyl, 4-hydroxy-1-piperidinyl, 4-(lower alkoxy)-1-piperidinyl, 4-morpholinyl or 2,6-di(-lower alkyl)-4-morpholinyl and either m and q are the integer 0 and n is the integer 1 or m and q are the integer 1 and n is the integer 0. In a special embodiment, m and q are the integer 0 and n is the integer 1. In another special embodiment, m and q are the integer 0, n is the integer 1 and $R^1$ is hydroxy or lower alkoxy.

The compounds listed hereinafter are preferred representatives of the class of substance characterized by formula I:

3-Methoxy-1-[(4-oxo-3-phenyl-4H-pyrido[2,1-a]phthalazin-1-yl)carbonyl]azetidine.

N,N-diethyl-4-oxo-3-phenyl-4H-pyrido[2,1-a]phthalazine-1-carboxamide,

4-[(4-oxo-3-phenyl-4H-pyrido[2,1-a]phthalazin-1-yl)carbonyl]morpholine, (S)-2-(methoxymethyl)-1-[(10-chloro-4-oxo-3-phenyl-4H-pyrido[2,1-a]phthalazin-1-yl)carbonyl]pyrrolidine, N-ethyl-N-(2-methoxyethyl)-10-chloro-4-oxo-3-phenyl-4H-pyrido[2,1-a]phthalazine-1-carboxamide, 1-[(10-chloro-4-oxo-3-phenyl-4H-pyrido[2,1-a]phthalazin-1-yl)carbonyl]-3-methoxyazetidine, N,N-dimethyl-10-chloro-4-oxo-3-phenyl-4H-pyrido[2,1-a]phthalazine-1-carboxamide.

N,N-diethyl-10-chloro-4-oxo-3-phenyl-4H-pyrido[2,1-a]phthalazine-1-carboxamide,

4-[(10-chloro-4-oxo-3-phenyl-4H-pyrido[2,1-a]phthalazin-1-yl)carbonyl]morpholine, rac-3-methoxy-1-[(10-chloro-4-oxo-3-phenyl-4H-pyrido[2,1-a]phthalazin-1-yl)carbonyl]pyrrolidine, (R)-2-(methoxymethyl)-1-[(10-chloro-4-oxo-3-phenyl-4H-pyrido[2,1-a]phthalazin-1-yl)carbonyl]pyrrolidine, N,N-diethyl-7-oxo-8-phenyl-7H-pyrido[1,2-b]thieno[2,3-d]pyridazine-10-carboxamide, 3-methoxy-1-[(7-oxo-8-phenyl-7H-pyrido[1,2-b]thieno[2,3-d]pyridazin-10-yl)carbonyl]azetidine, cis-2,6-dimethyl-4-[(7-oxo-8-phenyl-7H-pyrido[1,2-b]thieno[2,3-d]pyridazin-10-yl)carbonyl]morpholine, (R)-2-(methoxymethyl)-1-[(7-oxo-8-phenyl-7H-pyrido[1,2-b]thieno[2,3-d]pyridazin-10-yl)carbonyl]pyrrolidine, (S)-2-(methoxymethyl)-1-[(7-oxo-8-phenyl-7H-pyrido[1,2-b]thieno[2,3-d]pyridazin-10-yl)carbonyl]pyrrolidine, rac-3-methoxy-1-[(7-oxo-8-phenyl-7H-pyrido[1,2-b]thieno[2,3-d]pyridazin-10-yl)carbonyl]pyrrolidine, N-(2-methoxyethyl)-7-oxo-8-phenyl-7H-pyrido[1,2-b]thieno[2,3-d]pyridazine-10-carboxamide, 4-[(7-oxo-8-phenyl-7H-pyrido[1,2-b]thieno[2,3-d]pyridazin-10-yl)carbonyl]morpholine, N-ethyl-N-(2-methoxyethyl)-7-oxo-8-phenyl-7H-pyrido[1,2-b]thieno[2,3-d]pyridazine-10-carboxamide, N-(3-methoxypropyl)-7-oxo-8-phenyl-7H-pyrido[1,2-b]thieno[2,3-d]pyridazine-10-carboxamide, N,N-dimethyl-7-oxo-8-phenyl-7H-pyrido[1,2-d]thieno[2,3-d]pyridazine-10-carboxamide and N-methyl-7-oxo-8-phenyl-7H-pyrido[1,2-b]thieno[2,3-d]pyridazine-10-carboxamide.

Further representatives of the class of substance according to the present invention are:

Methyl 4-oxo-3-phenyl-4H-pyrido[2,1-a]phthalazine-1-carboxylate, methyl 7-oxo-8-phenyl-7H-pyrido[1,2-b]thieno[2,3-d]pyridazine-10-carboxylate, methyl 10-chloro-4-oxo-3-phenyl-4H-pyrido[2,1-a]phthalazine-1-carboxylate, 4-oxo-3-phenyl-4H-pyrido[2,1-a]phthalazine-1-carboxylic acid, 7-oxo-8-phenyl-7H-pyrido[1,2-b]thieno[2,3-d]pyridazine-10-carboxylic acid, 10-chloro-4-oxo-3-phenyl-4H-pyrido[2,1a]phthalazine-1-carboxylic acid, The compounds of formula I and the pharmaceutically acceptable acid addition salts of those which have basic substituent can be prepared in accordance with the invention by (a) reacting a compound of the formula

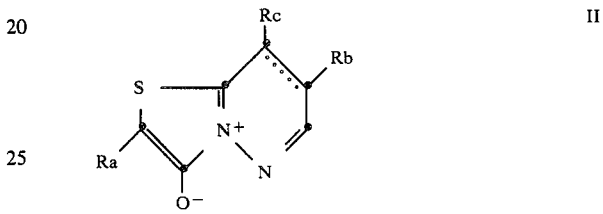

wherein Ra, Rb, Rc and the dotted line are as previously described, at an elevated temperature with a compound of the formula

or

wherein Rd' is cyano, nitro or the group of the formula —CO—$(Q^1A^2)_q$—$R^1$ and q, $A^2$, $Q^1$ and $R^1$ are as previously described, or with phenylvinyl sulfoxide and, if necessary, treating the cycloaddition product obtained with a strong base, or (b) reacting a compound of the general formula

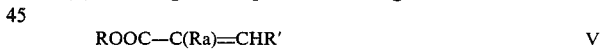

wherein R is lower alkyl, R' is hydrogen or lower alkyl and Ra is as previously described, at an elevated temperature when R' is hydrogen or in the presence of a strong base when R' is a lower alkoxy with a compound of the formula

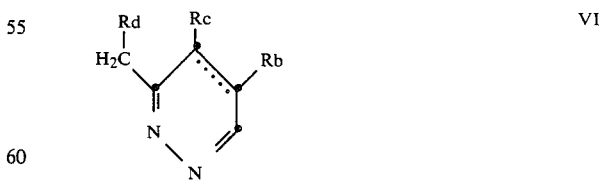

wherein Rb, Rc, Rd and the dotted line are as previously described, and dehydrogenating the cyclocondensation product obtained when R' is hydrogen, or (c) hydrolyzing a compound of formula I which contains an esterified carboxy group, or (d) esterifying a carboxylic acid of the formula

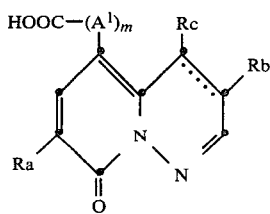

wherein $A^1$, Ra, Rb, Rc, m and the dotted line are as previously described, with an alcohol of the formula $$HO-A^{21}-R^1 \qquad VII$$

wherein $A^{21}$ is lower alkylene or a direct bond and $R^1$ is as previously described, or (e) converting a carboxylic acid of formula Ia above or a carboxylic acid of the formula

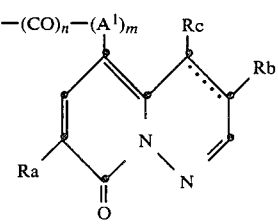

wherein $A^{22}$ is lower alkylene or the group —CO— and $R^{31}$ and $R^{41}$ together with the nitrogen atom is a 3- or 7-membered saturated N-heterocycle which is optionally substituted by one or two lower alkyl groups and which is substituted by a carboxyl group and which can contain as a ring member an oxygen or sulfur atom or the group $>N-R^5$, and $A^1$, $Q^1$, Ra, Rb, Rc, $R^5$, m, n, q and the dotted line are as previously described, or a reactive derivative thereof into the corresponding amide with, respectively, an amine of the formula $$HNR^2-A^{21}-R^1 \qquad IX$$

or $$HNR^3R^4 \qquad X$$

wherein $A^{21}$, $R^1$, $R^2$, $R^3$ and $R^4$ are as previously described, or with ammonia or a mono- or di(lower alkyl)amine, or (f) reacting a compound of the formula

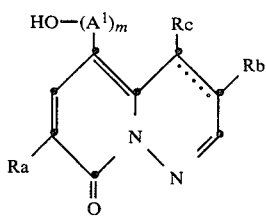

wherein $A^1$, Ra, Rb, Rc, m and the dotted line are as previously described, in the presence of a base with a compound of the formula $$X-A^{21}-R^1 \qquad XI$$

wherein X is a leaving group and $R^{21}$ and $R^1$ are as previously described, or reacting a compound of formula I which contains a free hydroxy group with a compound of the formula $$R-X \qquad XII$$

wherein R is lower alkyl and X are as previously described, or (g) reacting a compound of the formula

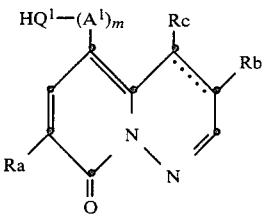

wherein $A^1$, $Q^1$, Ra, Rb, Rc, m and the dotted line are as previously described, in the presence of an acid-binding agent with a reactive derivative of a carboxylic acid of the formula $$R^1-COOH \qquad XIII$$

wherein $R^1$ is a previously described, or (h) reacting a compound of the formula

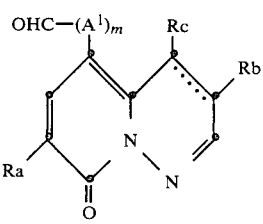

wherein $A^1$, Ra, Rb, Rc, m and the dotted line are as previously described, in the presence of a reducing agent with an amine of formula IX or X above, or (i) reducing a compound of the formula

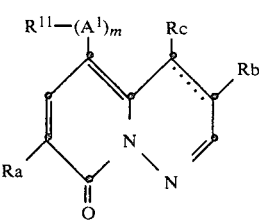

wherein $R^{11}$, is nitro, cyano or lower alkoxycarbonyl and $A^1$, Ra, Rb, Rc, m and the dotted line are as previously described, or a compound of formula Ia above or a reactive derivative thereof, or (j) oxidizing an alcohol of formula Ib' above or an alcohol of the formula

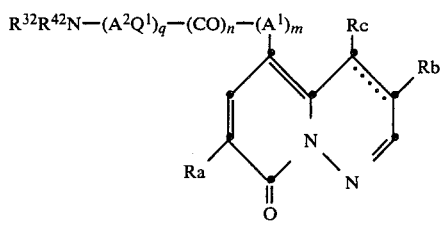   Ie wherein $A^1$, $A^2$, $Q^1$, Ra, Rb, Rc, m, n, q and the dotted line are as previously described, and $R^{32}$ and $R^{42}$ together with the nitrogen atom are a 3- to 7-membered, saturated N-heterocycle which is optionally substituted by one or two lower alkyl groups and which is substituted by a hydroxy group and which can contain as a ring member an oxygen or sulfur atom or the group $>N-R^5$, and $R^5$ is as previously described, or (k) reacting an isocyanate of the formula

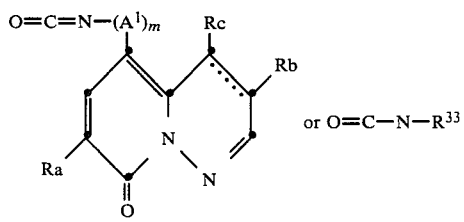   XIV wherein $A^1$, Ra, Rb, Rc, m and the dotted line are as previously described and $R^{33}$ is hydrogen, lower alkyl or ($C_{3-7}$)-cycloalkyl, with a lower alcohol or an amine of formula X above or with a compound of formula Ib above, or (l) reacting a compound of the formula

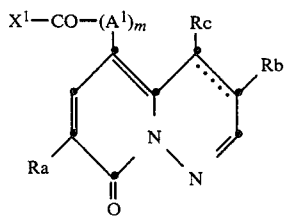   VIIIc wherein $X^1$ is a halogen atom and $A^1$, Ra, Rb, Rc, m and the dotted line are as previously described, with a lower alkylmagnesium halide, or (m) halogenating a compound of the formula

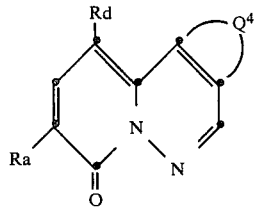   Ih wherein $Q^4$ is the group (a) or (b) above and Ra and Rd are as previously described, on the thiophene ring, or (n) reacting a compound of formula VIIIc above in the presence of a base with a compound of the formula

HYN=C(NH$_2$)—R''   XV,

H$_2$N—CHR''—CHR'''—Y'H   XVI or

H$_2$N—NH—C(R'')=Y''   XVII wherein Y is an oxygen atom or the group —NR'''—, Y' is an oxygen atom or the group —NH—, Y'' is an oxygen or sulfur atom and R'' and R''' each is hydrogen or lower alkyl, and cyclizing the product obtained, or (o) reacting a compound of the formula

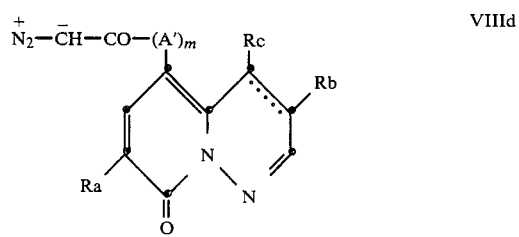   VIIId wherein A' is $C_{1-6}$-alkylene and Ra, Rb, Rc, the dotted line and m are as previously described, with a lower alcohol, or (p) decarboxylating a carboxylic acid of formula I in which m is the integer O, or (q) halogenating a compound of formula I in which Rd is hydrogen on the pyridone ring, or (r) cleaving the acetal group in a compound of the formula

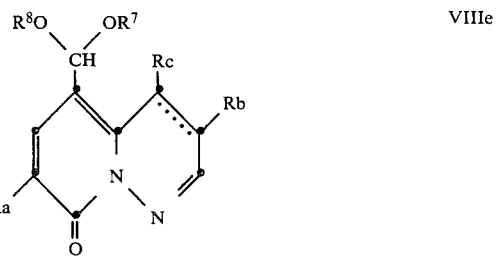   VIIIe wherein $R^7$ and $R^8$ each, independently, is lower alkyl or together are lower alkylene and Ra, Rb, Rc and the dotted line are as previously described, or (s) reacting a compound of the formula

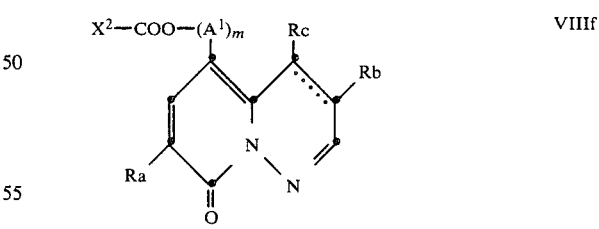   VIIIf wherein $X^2$ is phenoxy and $A^1$, Ra, Rb, Rc, the dotted line and m are as previously described, with an amine of formula X above, and (t) if desired, converting a compound of formula I obtained which has a basic substituent into a pharmaceutically acceptable acid addition salt.

In several of the above processes, in accordance with the invention, the reactive amino, carboxy and/or hydroxyl groups which may be present in the starting material must be blocked by protecting groups. These instances are readily recognizable by a person skilled in the art, and the choice of protecting groups which are suitable in a given case also present no difficulties to such a person.

Compounds of formula I in which Rd is hydrogen, cyano, nitro or the group of the formula —CO—(Q-$^1$A$^2$)q—R$^1$ and q, A$^2$, Q$^1$ and R$^1$ are as previously described, can be prepared in accordance with process variant (a). The reaction is conveniently effected in an inert solvent which boils at an elevated temperature, preferably above 80° C. Suitable solvents are, for example, aromatic hydrocarbons such as benzene, toluene and xylene, in which case the reaction is preferably carried out at the reflux temperature of the solvent.

When the reaction of a compound of formula II with a compound of formula III or with phenylvinyl sulfoxide is carried out at an elevated temperature, the corresponding compound of formula I is obtained directly. When a compound of formula II is reacted with a compound of formula IV, there is obtained first as the cycloaddition product the corresponding epithio compound of the formula

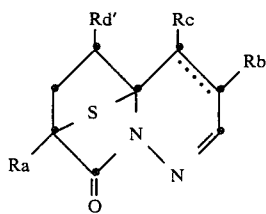

XVIII wherein Ra, Rb, Rc, Rd' and the dotted line are as previously described, which is subsequently converted into the corresponding compound of formula I by treatment with a strong base. Suitable bases are, for example, lower alkali metal alcoholates such as sodium methylate, in which case the corresponding alcohol is conveniently used as the solvent. The reaction is preferably carried out at the reflux temperature of the solvent.

The reaction of a compound of formula V, in which R' is hydrogen, with a compound of formula VI in accordance with process variant (b) can be carried out without a solvent or in the presence of a solvent which boils at an elevated temperature. Suitable solvents are, for example, aromatic hydrocarbons such as benzene, toluene and xylene. The cyclocondensation is, however, preferably carried out without a solvent at a temperature in the range of about 80° C. to about 150° C. The thus-obtained cyclocondensation product, namely a compound of the formula

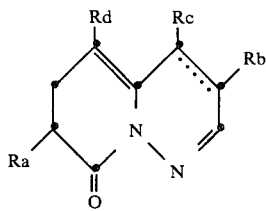

XIX wherein Ra, Rb, Rc, Rd and the dotted line are as previously described, is subsequently dehydrogenated with a suitable oxidation agent such as manganese dioxide. Suitable solvents are, for example, aromatic hydrocarbons such as benzene, toluene and xylene. The dehydrogenation is preferably carried out at a temperature in the range of about room temperature to the boiling temperature of the chosen solvent, preferably at the boiling temperature.

By reacting a compound of formula V, in which R' is lower alkoxy, in the presence of a strong base such as sodium hydride and in an inert solvent, preferably in an ether such as tetrahydrofuran, with a compound of formula VI in accordance with process variant (b), there is obtained the corresponding compound of formula I. The reaction temperature lies in the range of room temperature to the boiling temperature of the reaction mixture.

The compounds of formula XVIII, insofar as Rd' has a significance other than acetyl and ethoxycarbonyl, when Ra is phenyl, Rb and Rc together are the group —CH=CH—CH=CH— and the dotted line is an additional bond, and the compounds of formula XIX also form part of the invention.

Compounds of formula I which contain an esterified carboxy group can be hydrolyzed in accordance with process variant (c), whereby the corresponding free carboxylic acids are obtained. The hydrolysis can be carried out according to known methods. The hydrolysis is preferably carried out with an alkali metal hydroxide such as sodium hydroxide and potassium hydroxide in a lower alcohol such as methanol and ethanol or in a mixture of a lower alcohol and water. The reaction temperature conveniently lies in a range of room temperature to the boiling temperature of the reaction mixture, preferably at the boiling temperature of the reaction mixture.

Compounds of formula I in which Rd is the group of the formula —(A$^1$)$_m$—CO—O—A$^{21}$—R$^1$ and A$^1$, A$^{21}$, R$^1$ and m are as previously described can be prepared by esterifying a carboxylic acid of formula Ia with an alcohol of formula VII in accordance with process variant (d). The esterification can be carried out, for example, in the presence of an esterification reagent in an inert organic solvent. Suitable reagents are, for example, N-methyl-2-chloropyridinium iodide and the like, organic sulfonic acid halides such as methylsulfonyl chloride, p-toluenesulfonyl chloride and mesitylenesulfonyl chloride, and the like. Suitable solvents are, for example, halogenated hydrocarbons such as methylene chloride, chloroform and the like. Suitable bases are, for example, tertiary amines such as triethylamine, tri-n-butylamine and the like. The reaction is preferably carried out at a temperature in the range of room temperature to the reflux temperature of the solvent.

The desired esterification can also be carried out by firstly converting and carboxylic acid of formula Ia into a reactive derivative and then reacting the latter with an alcohol of formula VIII in the presence of a base. The corresponding carboxylic acid chlorides are preferably used as the reactive derivatives. Suitable bases are, for example, the tertiary amines mentioned previously. The reaction is preferably carried out at a temperature in the range of about room temperature to the reflux temperature of the reaction mixture, conveniently at room temperature.

The esterification with an alcohol of formula VII in which A$^{21}$ is lower alkylene and R$^1$ is hydrogen, that is, with a lower alcohol, can also be carried out by reacting the carboxylic acid with a N,N-dimethylformamide di(lower alkyl)acetal. The reaction with a N,N-dimethylformamide di(lower alkyl)acetal is preferably carried out in an inert solvent, for example, in an aromatic hydrocarbon such as benzene, at the reflux temperature of the reaction mixture.

Compounds of formula I in which Rd is the group $-(A^1)_m-CO-NR^2-A^{21}-R^1$ or $-(A^1)_m-CO-NR^3R^4$ and $A^1$, $A^{21}$, $R^1$, $R^2$, $R^3$, $RHU 4$ and m are as previously described can be prepared by reacting a carboxylic acid of formula Ia or a reactive derivative thereof with an amine of formula IX or X in accordance with process variant (e).

By reacting a carboxylic acid of formula VIIIa or a reactive derivative thereof with ammonia of a mono- or di(lower alkyl)amine in accordance with process variant (e), there can be prepared corresponding compounds of formula I in which $R^1$ is a group of the formula $-NR^3R^4$, wherein $R^3$ and $R^4$ together with the nitrogen are a 3- to 7-membered, saturated N-heterocycle which is optionally substituted by one or two lower alkyl groups and which is substituted by a carbamoyl or mono- or di(lower alkyl)carbamoyl group and which can contain as a ring member an oxygen or sulfur atom or the group $>N-R^5$ and $R^5$ is as previously described.

If the free carboxylic acid of formula Ia or VIIIa is used as the starting material, then the amidation reaction is preferably carried out in the presence of a condensation agent such as N-methyl-2-chloropyridinium iodide in an inert organic solvent and in the presence of a base. Suitable solvents are, for example, aromatic hydrocarbons such as benzene, toluene and xylene. Suitable bases are, for example, the tertiary amines mentioned above. Preferred reactive carboxylic acid derivatives which can be reacted in the presence of a base directly with the corresponding amine are the corresponding carboxylic acid chlorides. Suitable bases are again the previously mentioned tertiary amines. Suitable solvents are, for example, aromatic hydrocarbons such as benzene, toluene and xylene and ethers such as dioxane. In both cases, the reaction is preferably carried out at a temperature in the range of room temperature to the reflux temperature of the reaction mixture.

In accordance with process variant (f), there can be obtained on the one hand compounds of formula I in which Rd is a group of the formula $-(A^1)_m-O-A^{21}-R^1$ and $A^1$, $A^{21}$, $R^1$ and m are as previously described and on the other hand compounds of formula I which contain a hydroxy group etherified in the form of a lower alkyl ether.

The reaction of a compound of formula Ib' with a compound of formula XI or the reaction of a compound of formula I which contains a free hydroxy group with a compound of formula XII is conveniently carried out in an inert organic solvent such as N,N-dimethylformamide or the like, with a strong base, for example, an alkali metal hydride or hydroxide such as sodium hydride, potassium hydroxide and sodium hydroxide conveniently being used as the base. The reaction is conveniently carried out at a temperature in the range of 0° C. to room temperature. The leaving group denoted by X is preferably a halogen atom, especially a chlorine, bromine or iodine atom, or an alkylsulfonyloxy or arylsulfonyloxy group, for example, a methanesulfonyloxy or p-toluenesulfonyloxy group. In the preparation of lower alkyl ethers, X can also be a lower alkoxysulfonyloxy group, that is, the alkylating agent in this case is a di(lower alkyl) sulfate such as dimethyl sulfate.

Compounds of formula I in which Rd is a group of the formula $-(A^1)_m-Q^1-CO-R^1$ and $A^1$, $Q^1$, $R^1$ and m are as previously described can be prepared in accordance with process variant (g).

The reaction of a compound of formula Ib with a reactive derivative of a carboxylic acid of formula XIII, for example, a carboxylic acid chloride, is conveniently carried out in an inert organic solvent in the presence of an acid-binding agent, for example, a tertiary amine. Suitable solvents are, for example, aromatic hydrocarbons such as benzene, toluene and xylene and halogenated hydrocarbons such as methylene chloride. When $R^1$ is lower alkyl, corresponding carboxylic acid anhydrides can also be used, and in this case pyridine conveniently is used as the solvent and as the acid-binding agent. The reaction is preferably carried out at a temperature in the range of about 0° C. to the boiling temperature of the solvent.

Compounds of formula I in which Rd is a group of the formula $-(A^1)_m-CH_2-NR^2A^{21}-R^1$ or $-(A^1)_m-CH_2-NR^3R^4$ and $A^1$, $A^{21}$, $R^1$, $R^2$, $R^3$, $R^4$ and m are as previously described can be prepared in accordance with process variant (h). The reaction is preferably carried out in a lower alcohol as the solvent and with sodium cyanoborohydride as the reduction agent. The reaction is conveniently carried out at room temperature and the amine is conveniently used in the form of its hydrochloride.

Compounds of formula I in which Rd is a group of the formula $-(A^1)_m-R^{12}$ and $R^{12}$ is amino, aminomethyl, hydroxymethyl or methyl and $A^1$ and m are as previously described can be prepared in accordance with process variant (i). The choice of the suitable reduction agent depends on the one hand on the starting material which is used and on the other hand on the product which is desired. A compound of formula Id in which $R^{11}$ is cyano can, for example, be reduced with diborane in tetrahydrofuran to the corresponding aminomethyl compound. A compound of formula Id in which $R^{11}$ is nitro can, for example, be reduced with sodium sulfide in a lower alcohol such as methanol to the corresponding amino compound. A compound of formula Id in which $R^{11}$ is lower alkoxycarbonyl can be reduced with lithium borohydride to the corresponding hydroxymethyl compound and the acid chloride of a compound of formula Ia can be reduced with sodium borohydride in tetrahydrofuran and/or dimethylformamide to the corresponding hydroxymethyl compound. A carboxylic acid of formula Ia can, for example, be reduced with borane/tetrahydrofuran complex or borane/methyl sulfide complex in tetrahydrofuran to the corresponding methyl compound.

Compounds of formula I in which Rd is a group of the formula $-(A^1)_m-CHO$ or $-(A^1)_m-(CO)_n-(Q^1A^2)_q-NR^{34}R^{44}$ and $R^{34}$ and $R^{44}$ together are a 3- to 7-membered, saturated N-heterocycle which is optionally substituted by one or two lower alkyl groups and by an oxo group and which can contain as a ring member an oxygen or sulfur atom or the group $>N-R^5$, and $A^1$, $A^2$, $Q^1$, $R^5$, m, n and q are previously described can be prepared in accordance with process variant (j). The oxidation of alcohols of formula Ib' and Ie can be carried out according to known methods. For example, the desired oxidation can be carried out with manganese dioxide in a halogenated hydrocarbon such as methylene chloride at room temperature. The desired oxidation can, however, also be carried out with pyridinium chlorochromate in a halogenated hydrocarbon such as methylene chloride at room temperature or with dimethyl sulfoxide/trifluoroacetic acid anhydride in a halogenated hydrocarbon such as methylene chloride at temperatures of about −70° C.

Compounds of formula I in which Rd is a group of the formula $-(A^1)_m-NHCO-R^{13}$, $-(A^1)_m-NH-CO-NR^3R^4$ or $-(A^1)_m-Q^1-CO-NH-R^{33}$ and $R^{13}$ is lower alkoxy, and $A^1$, $Q^1$, $R^3$, $R^{33}$, $R^4$ and m are as previously described can be prepared in accordance with process variant (k) by reacting an isocyanate of formula VIIIb with a lower alcohol or an amine of formula X or by reacting an isocyanate of formula XIV with a compound of formula Ib. This reaction is conveniently carried out in an inert solvent, for example, in an aromatic hydrocarbon such as benzene, toluene or xylene, in a halogenated hydrocarbon such as methylene chloride or in an ether such as dioxane. The reaction is preferably carried out at a temperature in the range of about room temperature to the boiling temperature of the reaction mixture. If an isocyanate of formula XIV in which $R^{33}$ is hydrogen is used as the starting material, then this is conveniently used in protected form. An especially suitable protecting group in this case is the trichloroacetyl group which can be removed by hydrolysis, for example with potassium carbonate in water, after the reaction has been carried out.

Compounds of formula I in which Rd is a group of the formula $-(A^1)_m-CO-R^{14}$ and $R^{14}$ is lower alkyl, and $A^1$ and m are as previously described, can be prepared in accordance with process variant (1). Ethers such as tetrahydrofuran are preferably used as the solvent. The reaction is preferably carried out at a temperature in the range of $-78°$ C. to room temperature.

Compounds of formula I in which Rb and Rc together with the carbon atom denoted as $\alpha$ is a group of the formula $>C_\alpha-S-CH=CH-$ (h) or $>C_\alpha-CH=CH-S-$ (i) which is substituted by halogen and the dotted line is an additional bond can be prepared in accordance with process variant (m). Elemental halogen, for example elemental bromine, is preferably used as the halogenating agent. Suitable solvents are, for example, halogenated hydrocarbons such as chloroform. The halogenation is conveniently carried out in a temperature range of 0° C. to about room temperature.

Compounds of formula I in which Rd is a group of the formula $-(A^1)_m-R^-$ and $R^{15}$ are a 5-membered, partially unsaturated or aromatic heterocycle which is attached via a carbon atom and which is optionally substituted by one or two lower alkyl groups and $A^1$ and m are as previously described can be prepared in accordance with process variant (n). The reaction of a compound of formula VIIIc with a compound of formula XVI, XVII or XVIII is conveniently carried out in an inert solvent, for example, in an halogenated hydrocarbon such as methylene chloride or in an aromatic hydrocarbon such as benzene, toluene or xylene, and at a temperature in the range of about 0° C. to the reflux temperature of the reaction mixture. Suitable bases are, for example, the tertiary amines mentioned previously. The cyclization of the thus obtained product can be carried out according to known methods and which are familiar to any person skilled in the art. The cyclization can be carried out, for example, in the presence of catalytic amounts of a strong acid such as p-toluenesulfonic acid while removing the reaction water which is formed by means of a withdrawing agent such as toluene. However, the cyclization can also be carried out by means of diethyl azodicarboxylate/triphenylphosphine in an ether such as tetrahydrofuran.

Compounds of formula I in which Rd is a group of the formula $-(A')_m-CH_2-R^{16}$, A' is $C_{1-6}$-alkyl and $R^{16}$ is lower alkoxycarbonyl and m are as previously described can be prepared in accordance with process variant (o). The reaction of a diazoketone of formula VIIId with a lower alcohol is preferably carried out in the presence of a silver catalyst such as silver oxide, the lower alcohol being preferably used as the solvent. The reaction is carried out at an elevated temperature, preferably at the boiling temperature of the reaction mixture.

Compounds of formula I in which Rd is hydrogen can be prepared in accordance with process variant (p). The decarboxylation of a carboxylic acid of formula Ia is preferably carried out by dry heating, especially by dry heating in a vacuo to temperatures of about 200° to about 300° C.

Compounds of formula I in which Rd is halogen can be prepared in accordance with process variant (q). Suitable halogenating agents for the present halogenation are N-haloimides and N-haloamides such as N-chlorosuccinimide, N-bromosuccinimide, N-chloroacetamide and the like. A halogenated hydrocarbon such as methylene chloride, chloroform, carbon tetrachloride and the like is preferably used as the solvent. The reaction can be carried out in a temperature range of about 0° C. to the boiling temperature of the reaction mixture. The reaction is preferably carried out at room temperature.

Compounds of formula I in which Rd is the group —CHO can be prepared by cleaving the acetal group in a compound of formula VIIIe in accordance with process variant (r). The cleavage is preferably carried out by transacetalization in the presence of an acid such as p-toluenesulphonic acid and a ketone such as cyclohexanone, acetone and the like. The reaction can be carried out at a temperature in the range of room temperature to the boiling temperature of the reaction mixture.

Compounds of formula I in which $R^1$ is a group of the formula $-(A^1)_m-OCO-NR^3R^4$ can be prepared in accordance with process variants). Suitable solvents for the present purpose are, for example, ethers such as tetrahydrofuran, dioxan and diethyl ether, N,N-dimethylformamide and dimethyl sulfoxide. The reaction is conveniently carried out at room temperature.

Compounds of formula I which have one or more basic substituents can be converted into pharmaceutically acceptable acid addition salts in accordance with process variant (t). Such acid addition salts can be prepared according to known methods which are and familiar to any person skilled in the art. There come into consideration not only salts with inorganic acids, but also salts with organic acids, for example hydrochlorides, hydrobromides, sulfates, nitrates, citrates, acetates, maleates, succinates, methanesulfonates, p-tolueneslfonates and the like.

The compounds of formula II (insofar as Ra are other than phenyl when Rb and Rc together is the group $-CH=CH-CH=CH-$ and the dotted line is an additional bond), VIIIa, VIIIb, VIIIc, VIIId, VIIIe and VIIIf, which are used as starting materials, also form part of the present invention. These substances can be prepared as described hereinafter.

The novel compounds of formula II can be prepared, for example, by reacting a compound of the formula

XXI

[Structure: pyrimidine-like ring with Rc, Rb, S, N, H, N substituents and dotted line]

wherein Rb, Rc and the dotted line have the above significance, with a compound of the formula Ra—CHX²—COX¹   or   [epoxide-like structure with Ra, CN, CN]

XXII                        XXIII wherein $X^1$ and $X^2$ each is halogen and $R^1$ are as previously described. The reaction of a compound of formula XXI with a compound of formula XXII in which $X^1$ preferably is chlorine and $X^2$ preferably is bromine is preferably carried out at room temperature in a halogenated hydrocarbon such as chloroform, whereupon treatment is carried out with a basic amine such as triethylamine. The reaction of a compound of formula XXI with a compound of formula XXIII is preferably carried out in an inert solvent such as acetone, N,N-dimethylformamide, dimethyl sulfoxide and the like at room temperature.

The carboxylic acids of formula VIIIa can be prepared by hydrolyzing the corresponding lower alkyl esters of formula I. This hydrolysis can be carried out according to known methods, for example, in analogy to process variant (c).

The isocyanates of formula VIIIb can be prepared by treating a compound of formula Ib in which $Q^1$ is the group of the formula —NH— in an inert solvent with phosgene. Suitable solvents are, for example, halogenated hydrocarbons such as chloroform and 1,2-dichloroethane. However, the isocyanates of formula VIIIb can also be prepared by converting a carboxylic acid halide of formula VIIIc in an inert organic solvent with an azide such as sodium azide or trimethylsilyl azide into the corresponding carboxylic acid azide and rearranging this to the corresponding isocyanate by heating. Suitable solvents are, for example, ethers such as dioxane, ethylene glycol dimethyl ether, diethylene glycol dimethyl ether and the like, ketones such as ethyl methyl ketone and the like. The rearrangement is carried out at temperatures of 80° C. and above.

The carboxylic acid halides of formula VIIIc can be prepared by treating a carboxylic acid of formula Ia with a halogenating agent. Suitable halogenating agents are, for example, thionyl chloride, oxalyl chloride, phosphorus pentachloride and the like. In a preferred embodiment excess thionyl chloride is used and the reaction is carried out without an additional solvent at room temperature.

The diazoketones of formula VIIId can be prepared by reacting a carboxylic acid halide of formula VIIIc in an inert organic solvent with diazomethane. Suitable solvents are, for example, ethers such as tetrahydrofuran, dioxane and diethyl ether. The reaction is preferably carried out at a temperature in the range of about 0° to about 10° C.

The compounds of formula VIIIe can be prepared in analogy to process variant (a), there being used as the starting material a compound of the general formula HC≡C—CH(OR⁷)OR⁸ in which $R^7$ and $R^8$ are as previously described.

The compounds of formula VIIIf can be prepared by reacting a compound of formula Ib' in an inert solvent, for example, in an ether such as dioxane, and in the presence of a base, for example, a basic amine such as pyridine, with phenyl chloroformate.

The remaining compounds which are used as starting materials belong to classes of known substance.

As mentioned earlier, the compounds of formula I have valuable pharmacological properties. In particular, they display pronounced muscle relaxant, sedative-hypnotic, anticonvulsive and/or anxiolytic properties and have only a low toxicity. These properties can be demonstrated, for example, in the antipentetrazole test which is described hereinafter and which is generally recognized for recording such properties.

In this animal experiment the compound under investigation is administered orally to mice and 30 minutes later there are administered intraperitoneally 120 mg/kg of pentetrazole, which causes emprosthotonus and tonic stretchings of the fore and/or hind limbs in unprotected animals 1–4 minutes after the injection. 10 experimental animals are used per dosage of test substance. After counting the protected experimental animals the $ED_{50}$ is determined according to the Probit method. The $ED_{50}$ is that dosage which protects 50% of the experimental animals from the spasmodic seizures caused by pentetrazole. The results which have been obtained with representative members of the class of compound defined by formula I in the experiment described previously are compiled in the following Table. Moreover, the Table contains data concerning the acute toxicity ($LD_{50}$) of some of these compounds in mg/kg in the case of single oral administration to mice.

TABLE

| Compound | $ED_{50}$ in mg/kg p.o. | $LD_{50}$ in mg/kg p.o. |
|---|---|---|
| A | 1.1 | 1500 |
| F | 0.79 | 5000 |
| G | 0.08 | 5000 |
| H | 0.66 | >4000 |
| M | 0.83 | 5000 |

A = 3-Methoxy-1-[(4-oxo-3-phenyl-4H—pyrido[2,1-a]phthalazin-1-yl)carbonyl]azetidine
F = 1-[(10-Chloro-4-oxo-3-phenyl-4H—pyrido[2,1-a]phthalazin-1-yl)carbonyl]-3-methoxyazetidine
G = N,N—Dimethyl-10-chloro-4-oxo-3-phenyl-4H—pyrido[2,1-a]- phthalazine-1-carboxamide
H = N,N—Diethyl-10-chloro-4-oxo-3-phenyl-4H—pyrido[2,1-a]-phthalazine-1-carboxamide
M = 3-Methoxy-1[(7-oxo-8-phenyl-7H—pyrido[1,2-b]thieno-[2,3-d]pyridazin-10-yl)carbonyl]azetidine.

The compounds of formula I and the pharmaceutically acceptable acid addition salts of compounds of formula I which have a basic substituent can be used as medicaments, for example, in the form of pharmaceutical preparations. The pharmaceutical preparations can be administered orally, for example, in the form of tablets, coated tablets, dragees, hard and soft gelatin capsules, solutions, emulsions or suspension. However, the administration can also be carried out rectally, for example, in the form of suppositories, or parenterally, for example, in the form of injection solutions.

For the manufacture of pharmaceutical preparations, the products in accordance with the invention can be processed with pharmaceutically inert, inorganic or organic carriers. Lactose, maize starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, generally required in the case of soft gelatine capsules. Suitable carriers for the manufacture of solutions and syrups are, for example, water, polyols, saccharose, invert sugar, glucose and the like. Suitable carriers for injection solutions are, for example, water, alcohols, polyols, glycerine, vegetable oils and the like. Suitable carriers for suppositories are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically valuable substances. Medicaments containing a product in accordance with the invention and a therapeutically inert carrier as well as a process for their manufacture, which comprises bringing a product in accordance with the invention and, if desired, one or more other therapeutically valuable substances into a galenical administration form, are also objects of the present invention.

As mentioned earlier, the products in accordance with the invention can be used in the control or prevention of illnesses, especially in the control of convulsions and anxiety states, as well as for the manufacture of medicaments with muscle relaxant, sedative-hypnotic, anticonvulsive and/or anxiolytic properties. The dosage can vary within wide limits and is, of course, fitted to the individual requirements in each particular case. In the case of oral administration the daily dosage lies in a range of about 1 mg to about 100 mg.

The following Examples illustrate the present invention in more detail. However, they are not intended to limit its extent in any manner. All temperatures are given in degrees Celsius.

EXAMPLE 1

(I) 66.95 g of thieno[2,3-d]pyridazine-7(6H)-thione are suspended in 3200 ml of methylene chloride under argon, whereupon 102.7 g of α-bromophenylacetyl chloride are added dropwise thereto. The mixture is stirred at room temperature for about 30 minutes and then 121 ml of triethylamine are added dropwise thereto, whereby the mixture is cooled to 25°–30°. It is stirred for about 40 minutes. After evaporation of the solvent in vacuo the residue is taken up in 1000 ml of water and 200 ml of ether, whereupon the mixture is stirred for about 30 minutes. The separated crystals are filtered off under suction, washed with water and ether and dried overnight. The dried crystals are again triturated with 1000 ml of water. After suction filtration the red-violet crystals are washed with water and dried in vacuo. There is obtained 3-hydroxy-2-phenyl-thiazolo[3,2-b]thieno[2,3-d]pyridazin-4-ium hydroxide (internal salt) of m.p. 260°–264° (decomposition).

In an analogous manner,
(II) from 7-chloro-1(2H)-phthalazinethione and α-bromophenylacetyl chloride there is obtained, after recrystallization, 9-chloro-3-hydroxy-2-phenyl-thiazolo[2,3-a]phthalazin-4-ium hydroxide (internal salt) of m.p. 296°–298° (chloroform).

(a) 13.5 g of 3-hydroxy-2-phenylthiazolo[3,2-a]phthalazinium hydroxide (internal salt) and 8.1 ml of methyl propiolate are heated under reflux in 200 ml of toluene for 24 hours with the exclusion of moisture. The mixture is then left to cool and is stirred for 1 hour in an ice-bath. The crystals are filtered off under suction, dried and finally recrystallized from toluene. There is obtained methyl 4-oxo-3-phenyl-4H-pyrido[2,1-a]phthalazine-1-carboxylate as yellow crystals of m.p. 174°–175°.

In an analogous manner,
(b) from 3-hydroxy-2-phenylthiazolo[3,2-b]thieno[2,3-d]pyridazin-4-ium hydroxide (internal salt) and methyl propiolate there is obtained, after recrystallization from acetonitrile, methyl 7-oxo-8-phenyl-7H-pyrido[1,2-b]thieno[2,3-d]pyridazine-10-carboxylate as yellow crystals of m.p. 198°–199° and (c) from 9-chloro-3-hydroxy-2-phenylthiazolo[2,3-a]phthalazin-4-ium hydroxide (internal salt) and methyl propiolate there is obtained, after recrystallization from acetonitrile, methyl 10-chloro-4-oxo-3-phenyl-4H-pyrido[2,1-a]phthalazine-1-carboxylate as yellow crystals of m.p. 234°–236°.

EXAMPLE 2

(a) 11 g of methyl 4-oxo-3-phenyl-4H-pyrido[2,1-a]phthalazine-1-carboxylate are taken up in 300 ml of ethanol, whereupon a solution of 3.7 g of potassium hydroxide in 30 ml of water is added thereto and the mixture is heated under reflux until the reaction has finished. The reaction mixture is then cooled to room temperature and poured into 2200 ml of water. The mixture is adjusted to pH 7 by adding 1N aqueous hydrochloric acid and impurities are removed by two-fold extraction with 300 ml of methylene chloride each time. The aqueous phase is acidified to pH 1 with 2N aqueous hydrochloric acid and the crystals formed are filtered off under suction. After repeated washing with water and drying in vacuo there is obtained 4-oxo-3-phenyl-4H-pyrido[2,1-a]phthalazine-1-carboxylic acid as yellow crystals of m.p. 236°–237° (dec.).

In an analogous manner,
(b) from methyl 7-oxo-8-phenyl-7H-pyrido[1,2-b]thieno[2,3-d]phthalazine-1-carboxylate there is obtained, after recrystallization from dimethylformamide, 7-oxo-8-phenyl-7H-pyrido[1,2-b]thieno[2,3-d]pyridazine-10-carboxylic acid as yellow crystals of m.p. 262°–264° (decomposition) and (c) from methyl 10-chloro-4-oxo-3-phenyl-4H-pyrido[2,1-a]phthalazine-1-carboxylate there is obtained, after recrystallization from acetonitrile/dimethylformamide, 10-chloro-4-oxo-3-phenyl-4H-pyrido[2,1-a]phthalazine-1-carboxylic acid as yellow crystals of m.p. 242° (decomposition).

EXAMPLE 3

(a) 3.68 g of 4-oxo-3-phenyl-4H-pyrido[2,1-a]phthalazine-1-carboxylic acid are suspended in 80 ml of toluene with the exclusion of moisture, whereupon 5.1 ml of thionyl chloride and 0.2 ml of N,N-dimethylformamide are added thereto and the mixture is stirred at room temperature for 2 hours. The reaction mixture is evaporated in vacuo; the residue is taken up in toluene, whereupon the solution is again evaporated in vacuo. The thus-obtained pure carboxylic acid chloride is taken up in 90 ml of dioxan, whereupon there are added thereto in succession 6.52 ml of triethylamine and 1.4 g of 3-hydroxyazetidine hydrochloride. The mixture is stirred at room temperature until the reaction has finished. After removing the solvent in vacuo the residue is treated with a mixture of 200 ml of water and 100 ml of saturated aqueous sodium chloride solution, whereupon the mixture is cooled to about 2° and stirred for 30 minutes. The crystals are filtered off under suction and washed twice with 15 ml of water. The thus-obtained crystals are dried at 70° in vacuo. The aqueous phase is extracted three times with methylene chloride; the combined organic phases are washed once with 50 ml of water, dried over sodium sulfate, filtered and evaporated. The crystals are combined with the material obtained above and stirred in 150 ml of ether for 30 minutes. The ether is removed by filtration and the yellow crystals are dried. There is obtained 3-hydroxy-1-[(4-oxo-3-phenyl-4H-pyrido[2,1-a]phthalazin-1-yl)carbonyl]azetidine of m.p. 260°-264° (dec.).

In an analogous manner, from 4-oxo-3-phenyl-4H-pyrido[2,1-a]phthalazine-1-carboxylic acid and (b) diethylamine there is obtained N,N-diethyl-4-oxo-3-phenyl-4H-pyrido[2,1-a]phthalazine-1-carboxamide of m.p. 167° (ethyl acetate);

(c) morpholine there is obtained 4-[(4-oxo-3-phenyl-4H-pyrido[2,1-a]phthalazin-1-yl)carbonyl]morpholine of m.p. 246°-248° (acetonitrile).

EXAMPLE 4

In analogy to Example 3(a), from 7-oxo-8-phenyl-7H-pyrido[1,2-b]thieno[2,3-d]pyridazine-10-carboxylic acid and (a) diethylamine there is obtained N,N-diethyl-7-oxo-8-phenyl-7H-pyrido[1,2-b]thieno[2,3-d]pyridazine-10-carboxamide of m.p. 207°-209° (acetonitrile);

(b) 3-methoxyazetidine there is obtained 3-methoxy-1-[(7-oxo-8-phenyl-7H-pyrido[1,2-b]thieno[2,3-d]pyridazin-10-yl)carbonyl]azetidine of m.p. 209°-210° (ethanol);

(c) cis-2,6-dimethylmorpholine there is obtained cis-2,6-dimethyl-4-[(7-oxo-8-phenyl-7H-pyrido[1,2-b]thieno[2,3-d]pyridazin-10-yl)carbonyl]morpholine of m.p. 250°-252° (ethanol);

(d) (R)-prolinol there is obtained (R)-1-[(7-oxo-8-phenyl-7H-pyrido[1,2-b]thieno[2,3-d]pyridazin-10-yl)carbonyl]-2-pyrrolidinemethanol of m.p. 252°-254° (acetonitrile);

(e) (S)-prolinol there is obtained (S)-1-[(7-oxo-8-phenyl-7H-pyrido[1,2-b]thieno[2,3-d]pyridazin-10-yl)carbonyl]-2-pyrrolidinemethanol of m.p. 250°-253° (acetonitrile);

(f) (R)-2-(methoxymethyl)pyrrolidine there is obtained (R)-2-(methoxymethyl)-1-[(7-oxo-8-phenyl-7H-pyrido[1,2-b]thieno[2,3-d]pyridazin-10-yl)carbonyl]pyrrolidine of m.p. 195°-201° (ethanol);

(g) (S)-2-(methoxymethyl)-pyrrolidine there is obtained (S)-2-(methoxymethyl)-1-[(7-oxo-8-phenyl-7H-pyrido[1,2-b]thieno[2,3-]pyridazin-10-yl)carbonyl]pyrrolidine of m.p. 194°-197° (ethanol);

(h) rac-3-methoxy-pyrrolidine there is obtained rac-3-methoxy-1-[(7-oxo-8-phenyl-7H-pyrido[1,2-b]thieno-[2,3-d]pyridazin-10-yl)carbonyl]pyrrolidine of m.p. 231°-232° (ethanol);

(i) 2-methoxyethylamine there is obtained N-(2-methoxyethyl)-7-oxo-8-phenyl-7H-pyrido[1,2-b]thieno[2,3-d]pyridazine-10-carboxamide of m.p. 206°-208° (ethanol);

(j) morpholine there is obtained 4-[(7-oxo-8-phenyl-7H-pyrido[1,2-b]thieno[2,3-d]pyridazin-10-yl)carbonyl]morpholine of m.p. 246°-247° (ethanol);

(k) N-ethyl-N-(2-methoxyethyl)amine there is obtained N-ethyl-N-(2-methoxyethyl)-7-oxo-8-phenyl-7H-pyrido[1,2-b]thieo[2,3-d]pyridazine-10-carboxamide of m.p. 134°-136° (ethanol);

(l) 3-methoxypropylamine there is obtained N-(3-methoxypropyl)-7-oxo-8-phenyl-7H-pyrido[1,2-b]thieno[2,3-d]pyridazine-10-carboxamide of m.p. 226°-228° (ethanol);

(m) methylamine there is obtained N-methyl-7-oxo-8-phenyl-7H-pyrido[1,2-b]thieno[2,3-d]pyridazine-10-carboxamide of m.p. 304°-308° (dec.; dimethylformamide);

(n) N,N-dimethylamine there is obtained N,N-dimethyl-7-oxo-8-phenyl-7H-pyrido[1,2-b]thieno[2,3-d]pyridazine-10-carboxamide of m.p. 215°-217° (ethanol).

EXAMPLE 5

In analogy to Example 3(a), from 10-chloro-4-oxo-3-phenyl-4H-pyrido[2,1-a]phthalazine-1-carboxylic acid and (a) diethylamine there is obtained N,N-diethyl-10-chloro-4-oxo-3-phenyl-4H-pyrido[2,1-a]phthalazine-1-carboxamide of m.p. 212°-215° (acetonitrile);

(b) morpholine there is obtained 4-[10-chloro-4-oxo-3-phenyl-4H-pyrido[2,1-a]phthalazin-1-yl)carbonyl]-morpholine of m.p. 254°-257° (dimethylformamide);

(c) rac-3-methoxypyrrolidine there is obtained rac-3-methoxy-1-[(10-chloro-4-oxo-3-phenyl-4H-pyrido[2,1-a]phthalazin-1-yl)carbonyl]pyrrolidine of m.p. 203°-205° (acetonitrile);

(d) (R)-prolinol there is otained (R)-1-[(10-chloro-4-oxo-3-phenyl-4H-pyrido[2,1-a]phthalazin-1-yl)carbonyl]-2-pyrrolidinemethanol of m.p. 261°-264° (acetonitrile);

(e) (R)-2-(methoxymethyl)pyrrolidine there is obtained (R)-2-(methoxymethyl)-1-[(10-chloro-4-oxo-3-phenyl-4H-pyrido[2,1-a]phthalazin-1-yl(carbonyl)pyrrolidine of m.p. 160°-163° (ether/acetone/n-hexane);

(f) (S)-(2-methoxymethyl)pyrrolidine there is obtained (S)-2-(methoxymethyl)-1-[(10-chloro-4-oxo-3-phenyl-4H-pyrido[2,1-a]phthalazin-1-yl(carbonyl)pyrrolidine of m.p. 107°-110° (ether/acetone);

(g) N-ethyl-N-(2-methoxyethyl)amine there is obtained N-ethyl-N-(2-methoxyethyl)-10-chloro-4-oxo-3-phenyl-4H-pyrido[2,1-a]phthalazine-1-carboxamide of m.p. 167° (ethyl acetate);

(h) 3-methoxyazetidine there is obtained 1-[(10-chloro-4-oxo-3-phenyl-4H-pyrido[2,1-a]phthalazin-1-yl)carbonyl]-3-methoxyazetidine of m.p. 238°-240° (acetonitrile);

(i) dimethylamine there is obtained N,N-dimethyl-10-chloro-4-oxo-3-phenyl-4H-pyrido[2,1-a]phthalazine-1-carboxamide of m.p. 244°-246° (ethanol).

EXAMPLE 6

The acid chloride prepared from 2.58 g of 7-oxo-8-phenyl-7H-pyrido[1,2L -b[2,3-d]pyridazine-10-carboxylic acid in accordance with Example 3(a) is heated under reflux with 0.8 g of cyclopropanecarboxamide oxime in 50 ml of acetic acid until the reaction is complete. The solvent is removed in vacuo and the residue is chromatographed on silica gel. After recrystallization from ethyl acetate there are obtained 10-(3-cyclopropyl-1,2,4 oxadiazol-5-yl)-7-oxo-8-phenyl-7H-pyrido[1,2-b]thieno[2,3-d]pyridazine as yellow crystals of m.p.

201°–202° and 7-oxo-8-phenyl-7H-pyrido[1,2-d]pyridazine as yellow crystals of m.p. 242°–244° (acetonitrile).

EXAMPLE 7

3.15 g of 3-hydroxy-1-[(4-oxo-3-phenyl-4H-pyrido[2,1-a]phthalazin-1-yl)carbonyl]azetidine are suspended in 30 ml of N,N-dimethylformamide under argon, whereupon the mixture is cooled to 1°–3° in an ice-bath and 0.81 ml of methyl iodide and 0.81 g of powdered potassium hydroxide (content about 89%) are added thereto. The mixture is stirred in an ice-bath for 20 minutes, the same amounts of methyl iodide and potassium hydroxide are again added thereto and the mixture is stirred for an additional 20 minutes. The reaction mixture is poured into 150 ml of ice/water and adjusted to pH 5 with 2N aqueous hydrochloric acid. After repeated extraction with methylene chloride the organic phase is dried over sodium sulfate, filtered and evaporated. The residue is chromatographed on silica gel with methylene chloride/methanol (9:1). The thus-obtained crude product is recrystallized from ethanol. There is obtained 3-methoxy-1-[(4-oxo-3-phenyl)-4H-pyrido)[2,1-a]phthalazin-1-yl)carbonyl]azetidine as yellow crystals of m.p. 136°–138°.

EXAMPLE A

Compound A (3-methoxy-1-[(4-oxo-3-phenyl-4H-pyrido-[2,1-a]phthalazin-1-yl)carbonyl]azetidine) can be used in a known manner as the active substance for the manufacture of pharmaceutical preparations of the following composition:

| (a) Tablets | mg/tablet |
|---|---|
| Compound A | 5 |
| Lactose | 135 |
| Maize starch | 51 |
| Polyvinylpyrrolidone | 8 |
| Magnesium stearate | 1 |
| Tablet weight | 200 |

| (b) Capsules | mg/capsule |
|---|---|
| Compound A | 10 |
| Lactose | 30 |
| Maize starch | 8.5 |
| Talc | 1 |
| Magnesium stearate | 0.5 |
| Capsule fill weight | 50 |

The compounds listed hereinafter can also be used in place of compound A as the active substance for the manufacture of pharmaceutical preparations of the above composition:

Compound B: N,N-Diethyl-4-oxo-3-phenyl-4H-pyrido[2,1-a]phthalazine-1-carboxamide, Compound C: 4-[(4-Oxo-3-phenyl-4H-pyrido[2,1-a]phthalazin-1-yl)carbonyl]morpholine, Compound D: (S)-2-(Methoxymethyl)-1-[(10-chloro-4-oxo-3-phenyl-4H-pyrido[2,1-a]phthalazin-1-yl)carbonyl]pyrrolidine, Compound E: N-Ethyl-N-(2-methoxyethyl)-10-chloro-4-oxo-3-phenyl-4H-pyrido[2,1-a]phthalazine-1-carboxamide, Compound F: 1-[(10-Chloro-4-oxo-3-phenyl-4H-pyrido[2,1-a]phthalazin-1-yl)carbonyl]-3-methoxyazetidine, Compound G: N,N-Dimethyl-10-chloro-4-oxo-3-phenyl-4H-pyrido[2,1-a]phthalazine-1-carboxamide, Compound H: N,N-Diethyl-10-chloro-4-oxo-3-phenyl-4H-pyrido[2,1-a]phthalazine-1-carboxamide, Compound I: 4-[(10-Chloro-4-oxo-3-phenyl-4H-pyrido-[2,1-a]phthalazin-1-yl)carbonyl]morpholine, Compound J: rac-3-Methoxy-1-[(10-chloro-4-oxo-3-phenyl-4H-pyrido[2,1-a]pthalazin-1-yl)carbonyl]pyrrolidine, Compound K: (R)-2-(Methoxymethyl)-1-[(10-chloro-4-oxo-3-phenyl-4H-pyrido[2,1-a]phthalazin-1-yl)carbonyl]pyrrolidine, Compound L: N,N-Diethyl-7-oxo-8-phenyl-7H-pyrido[1,2-b]thieno[2,3-d]pyridazine-10-carboxamide, Compound M: 3-Methoxy-1-[(7-oxo-8-phenyl-7H-pyrido-[1,2-b]thieno[2,3-d]pyridazin-10-yl)carbonyl]azetidine, Compound N: cis-2,6-Dimethyl-4-[(7-oxo-8-phenyl-7H-pyrido[1,2-b]thieno[2,3-d]pyridazin-10-yl)carbonyl]morpholine, Compound O: (R)-2-(Methoxymethyl)-1-[(7-oxo-8-phenyl-7H-pyrido[1,2-b]thieno[2,3-d]pyridazin-10-yl)carbonyl]pyrrolidine, Compound P: (S)-2-(Methoxymethyl)-1-[(7-oxo-8-phenyl-7H-pyrido[1,2-b]thieno[2,3-d]pyridazin-10-yl)carbonyl]pyrrolidine, Compound Q: rac-3-Methoxy-1-[(7-oxo-8-phenyl-7H-pyrido[1,2-b]thieno[2,3-d]pyridazin-10-yl)carbonyl]pyrrolidine, Compound R: N-(2-Methoxyethyl)-7-oxo-8-phenyl-7H-pyrido[1,2-b]thieno[2,3-d]pyridazine-10-carboxamide, Compound S: 4-[(7-Oxo-8-phenyl-7H-pyrido[1,2-b]thieno[2,3-d]pyridazin-10-yl)carbonyl]morpholine, Compound T: N-ethyl-N-(2-methoxyethyl)-7-oxo-8-phenyl-7H-pyrido[1,2-b]thieno[2,3-d]pyridazine-10-carboxamide, Compound U: N-(3-Methoxypropyl)-7-oxo-8-phenyl-7H-pyrido[1,2-b]thieno[2,3-d]pyridazine-10-carboxamide, Compound V: N,N-Dimethyl-7-oxo-8-phenyl-7H-pyrido[1,2-b]thieno[2,3-d]pyridazine-10-carboxamide, Compound W: N-Methyl-7-oxo-8-phenyl-7H-pyrido[1,2-b]thieno[2,3-d]pyridazine-10-carboxamide and Compound X: Methyl 4-oxo-3-phenyl-4H-pyrido[2,1-a]phthalazine-1-carboxylate.

We claim:

1. A compound of the formula

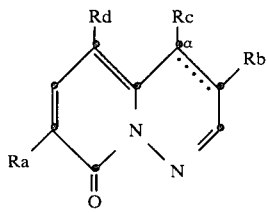

I wherein Ra is selected from the group consisting of unsubstituted phenyl, pyridyl or thienyl or said groups substituted by halogen, trifluoromethyl, nitro, lower alkyl or lower alkoxy, Rb and Rc together with the carbon atom denoted by α are a group of the formula >$C_a$—CH=CH—CH=CH— (c) which is unsubstituted or substituted by halogen, trifluoromethyl, lower alkyl, lower alkoxy, nitro, amino or mono- or di(lower alkyl)amino and the dotted line is an additional bond, Rd is the group of the formula —$(A^1)_m$—$(CO)_n$—$(Q^1A^2)_q$—$R^1$, m, n and q each are the integer 0 or 1, $A^1$ is lower alkylene, $A^2$ is lower alkylene, a direct bond or the group —CO—, $Q^1$ is an oxygen atom or the group —$NR^2$—, $R^1$ is hydrogen, hydroxy, cyano, nitro, halogen, lower alkoxy, lower alkyl, lower alkoxycarbonyl, phenyl group which is unsubstituted or substituted by halogen, trifluoromethyl, lower alkyl, lower alkoxy, nitro, amino or mono- or di(lower alkyl)amino, a group of the formula —$NR^3R^4$ or a 5-membered saturated, partially unsaturated or aromatic heterocycle which is attached via a carbon atom and contains as the hetero ring member(s) an oxygen or sulfur atom or an imino or lower alkylimino group and optionally one or two nitrogen atoms, and which is unsubstituted or substituted by one or two lower alkyl groups or substituted by a ($C_{3-6}$)-cycloalkyl, hydroxy, lower alkoxy, lower alkanoyloxy, lower hydroxyalkyl, lower alkoxyalkyl, lower alkanoyloxyalkyl, lower alkoxycarbonyl, loweralkanoyl, carbamoyl, mono- or di(lower alkyl)carbamoyl, oxo or alkylenedioxy group, $R^2$ is hydrogen, lower alkyl, or phenyl group which is unsubstituted or substituted by halogen, trifluoromethyl, lower alkyl, lower alkoxy, nitro, amino or mono- or di(lower alkyl)amino, $R^3$ and $R^4$ each is hydrogen, lower alkyl, lower alkoxyalkyl, lower dialkoxyalkyl, lower alkylenedioxyalkyl, lower cyanoalkyl, lower haloalkyl, lower hydroxyalkyl, lower dihydroxyalkyl, lower alkanoyl, lower alkoxycarbonyl or a ($C_{3-7}$)-cycloalkyl group which is unsubstituted or substituted by hydroxy, lower alkoxy, lower alkanoyloxy, lower hydroxyalkyl, lower alkoxyalkyl, lower alkanoyloxyalkyl, oxo, carbamoyl, mono- or di(lower alkyl)carbamoyl or by lower alkylenedioxy or $R^3$ and $R^4$ together with the nitrogen atom are a saturated N-heterocycle selected from 4,4-($C_{1-4}$alkylendioxy)-1-piperidinyl, or selected from the group consisting of unsubstituted 1-azetidinyl, 1-pyrrolidinyl, 1-piperidinyl, 4-morpholinyl, 4-thiomorpholinyl or 4-$R^5$-1-piperazinyl or substituted by one or two lower alkyl groups or one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- di(lower alkyl)carbamoyl, oxo or lower groups, and $R^5$ is hydrogen, lower alkyl, lower hydroxyalkyl, lower alkoxyalkyl, lower alkanoyloxyalkyl, lower alkanoyl, lower alkoxycarbonyl, carbamoyl, or mono- or di(lower alkyl)carbamoyl, with the provision that n is the integer 0 when q is the integer 1 and $A^2$ is the group —CO—, that $R^1$ is other than cyano, nitro, halogen or lower alkoxycarbonyl, when q is the integer 0 and n is the integer 1 or when q is the integer 1 and $A^2$ is the group —CO—, that $R^1$ is other than hydroxy, cyano, nitro, halogen, lower alkoxycarbonyl, lower alkoxy and —$NR^3R^4$ when q is the integer 1 and $A^2$ is a direct bond, or a pharmaceutically acceptable acid addition salt of compound of formula I which has one or more basic substituents.

2. A compound according to claim 1, wherein Rd is other than acetyl when Ra is phenyl, Rb and Rc together are the group —CH=CH—CH=CH— and the dotted line is an additional bond.

3. A compound according to claim 2, wherein Ra is phenyl.

4. A compound according to claim 3, wherein Rb and Rc together with the carbon atom denoted by α are a group of the formula >$C_\alpha$—CH=CH—CH=CH— which is unsubstituted or substituted by halogen and the dotted line is an additional bond.

5. A compound according to claim 4, wherein Rb and Rc together with the carbon atom denoted by α is the group of the formula >$C_\alpha$—CH=CCl—CH=CH—.

6. A compound according to claim 5, wherein $Q^1$ is an oxygen atom, $A^2$ is the group —CO—, $R^1$ is the group —$NR^3R^4$, $R^3$ is lower alkyl or lower alkoxyalkyl and $R^4$ is hydrogen or lower alkyl or $R^3$ and $R^4$ together with the nitrogen atom are a saturated N-heterocycle selected from the group consisting of unsubstituted 1-acetidinyl, 1-pyrrolidinyl, 1-piperidinyl or 4-morpholinyl or said groups maybe or substituted by one or two lower alkyl groups or a hydroxy, lower alkoxy, lower hydroxyalkyl or lower alkoxyalkyl group and either m and q are the integer 0 and n is the integer 1 or m and q are the integer 1 and n is the integer 0.

7. A compound according to claim 6, wherein $A^1$ is methylene and $R^3$ is lower alkyl or lower alkoxyalkyl and $R^4$ is hydrogen or lower alkyl or $R^3$ and $R^4$ together with the nitrogen atom are a 1-azetidinyl, 1-pyrrolidinyl, 1-piperidinyl or 4-morpholinyl group which is unsubstituted or subsubstituted by one or two lower alkyl groups or by a hydroxy, lower alkoxy, lower hydroxyalkyl or lower alkoxyalkyl group.

8. A compound according to claim 7, wherein $R^3$ is lower alkyl or 2-(lower alkoxy)ethyl and $R^4$ is hydrogen or lower alkyl or $R^3$ and $R^4$ together with the nitrogen atom are 3-(lower alkoxy)-1-azetidinyl, 3-(lower alkoxy)-1-pyrrolidinyl, 2-(lower alkoxyalkyl)-1-pyrrolidinyl, 2-(lower hydroxyalkyl)-1-pyrrolidinyl, 4-hydroxy-1-piperidinyl, 4-(lower alkoxy)-1-piperidinyl, 4-morpholinyl or 2,6-di(lower alkyl)-4-morpholinyl.

9. A compound according to claim 8, wherein m and q are the integer 0 and n is the integer 1.

10. A compound according to claim 5, wherein m and q are the integer 0, n is the integer 1 and $R^1$ is hydroxy or lower alkoxy.

11. A compound according to claim 1, 3-Methoxy-1-[(4-oxo-3-phenyl-4H-pyrido[2,1-a]-phthalazin-1-yl)carbonyl]acetidine.

12. A compound according to claim 1, N,N-Diethyl-4-oxo-3-phenyl-4H-pyrido[2,1-a]-phthalazine-1-carboxamide.

13. A compound according to claim 1, 4-[(4-Oxo-3-phenyl-4H-pyrido[2,1-a]phthalazin-1-yl)carbonyl]morpholine.

14. A compound according to claim 1, (S)-2-(Methoxymethyl)-1-[(10-chloro-4-oxo-3-phenyl-4H-pyrido[2,1-a]phthalazin-1-yl)carbonyl]-pyrrolidine.

15. A compound according to claim 1, N-Ethyl-N-(2-methoxyethyl)-10-chloro-4-oxo-3-phenyl-4H-pyrido[2,1-a]phthalazine-1-carboxamide.

16. A compound according to claim 1, 1-[(10-Chloro-4-oxo-3-phenyl-4H-pyrido[2,1-a]-phthalazin-1-yl)carbonyl]-3-methoxyazetidine.

17. A compound according to claim 1, N,N-Dimethyl-10-chloro-4-oxo-3-phenyl-4H-pyrido-[2,1-a]phthalazine-1-carboxamide.

18. A compound according to claim 1, N,N-Diethyl-10-chloro-4-oxo-3-phenyl-4H-pyrido-[2,1-a]phthalazine-1-carboxamide.

19. A compound according to claim 1, 4-[(10-Chloro-4-oxo-3-phenyl-4H-pyrido[2,1-a]-phthalazin-1-yl)carbonyl]morpholine.

20. A compound according to claim 1, rac-3-Methoxy-1-[(10-chloro-4-oxo-3-phenyl-4H-pyrido[2,1-a]phthalazin-1-yl)carbonyl]pyrrolidine.

21. A compound according to claim 1, (R)-2-(Methoxymethyl)-1-[(10-chloro-4-oxo-3-phenyl-4H-pyrido[2,1-a]phthalazin-1-yl)carbonyl]pyrrolidine.

22. A compound according to claim 1, Methyl 4-oxo-3-phenyl-4H-pyrido[2,1-a]phthalazine-1-carboxylate, methyl 7-oxo-8-phenyl-7H-pyrido[1,2-b]thieno[2,3-d]pyridazine-10-carboxylate, or methyl 10-chloro-4-oxo-3-phenyl-4H-pyrido[2,1-a]phthalazine-1-carboxylate.

23. A compound according to claim 1, 4-Oxo-3-phenyl-4H-pyrido[2,1-a]phthalazine-1-carboxylic acid, 7-oxo-8-phenyl-7H-pyrido[1,2-b]thieno[2,3-d]pyridazine-10-carboxylic acid, or 10-chloro-4-oxo-3-phenyl-4H-pyrido[2,1-a]phthalazine-1-carboxylic acid.

24. A compound according to claim 1, 3-Hydroxy-1-[(4-oxo-3-phenyl-4H-pyrido[2,1-a]-phthalazin-1-yl)carbonyl]azetidine, (R)-1-[(7-oxo-8-phenyl-7H-pyrido[1,2-b]thieno[2,3-d]pyridazin-10-yl)carbonyl]-2-pyrrolidinemethanol, (S)-1-[(7-oxo-8-phenyl-7H-pyrido[1,2-]thieno[2,3-d]pyridazin-10-yl)carbonyl]-2-pyrrolidinemethanol, or (R)-1-[(10-chloro-4-oxo-3-phenyl-4H-pyrido[2,1-a]phthalazin-1-yl)carbonyl]-2-pyrrolidinemethanol.

25. A compound of the formula

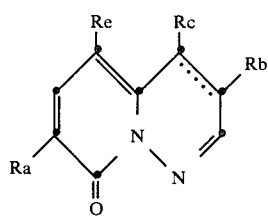
VIII wherein Re is the group —$(A^1)_m$—OOC—$X^2$, —$(A^1)_m$—$(CO)_n$—$(Q^1A^{22})_q$—$NR^{31}R^{41}$, —$(A^1)_m$—N=C=O, —$(A^1)_m$—CO—$X^1$, —$(A')_m$—(CO)——CH——$N_2^+$ or —CH($OR^7$)$OR^8$, A' is lower alkylene, Q' is an oxygen atom or the group —$NR^2$— wherein $R^2$ is hydrogen, lower alkyl or aryl, Ra is selected from the group consisting of phenyl, pyridyl or thienyl or said group substituted by halogen, trifluoromethyl, nitro, lower alkyl or lower alkoxy, Rb and Rc together with the carbon atom denoted by α are a group of the formula or $C_\alpha$—CH=CH—CH=CH— (c) which is unsubstituted substituted by halogen, trifluoromethyl, lower alkyl, lower alkoxy, nitro, amino or mono- or di(lower alkyl)amino and the dotted line is an additional bond, and A' is $C_{1-6}$-alkylene, $A^{22}$ is lower alkylene or the group —CO—, $R^7$ and $R^8$ each are lower alkyl or together are lower alkylene, $R^{31}$ and $R^{41}$ together with a nitrogen atom are a saturated N-heterocycle selected from the group consisting of unsubstituted 1-azetidinyl, 1-pyrrolidinyl, 1-piperidinyl, 4-morpholinyl, 4-thiomorpholinyl or 4-R5-1-piperazinyl substituted by one or two lower alkyl groups and substituted by a carboxy group and which can contain as a ring member an oxygen or sulfur atom or the group —N—$R^5$ wherein $R^5$ is hydrogen, lower alkyl, lower hydroxy alkyl, lower alkoxyalkyl, lower alkanoyloxyalkyl, lower alkanoyl, lower alkoxycarbonyl, carbamoyl or mono- or di(lower alkyl)carbamoyl, $X^1$ is a halogen atom and $X^2$ is phenoxy.

26. A pharmaceutical composition comprising an effective amount of a compound of the formula

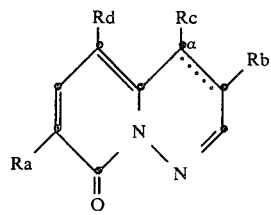
I wherein Ra is selected from the group consisting of unsubstituted phenyl, pyridyl or thienyl or said groups substituted by halogen, trifluoromethyl, nitro, lower alkyl or lower alkoxy, Rb and Rc together with the carbon atom denoted by α are a group of the formula >$C_\alpha$—CH=CH—CH=CH— (c) which is unsubstituted or substituted by halogen, trifluoromethyl, lower alkyl, lower alkoxy, nitro, amino or mono- or di(lower alkyl)amino and the dotted line is an additional bond, Rd is the group of the formula —$(A^1)_m$—$(CO)_n$—$(Q^1A^2)_q$—$R^1$, m, n and q each are the integer 0 or 1, $A^1$ is lower alkylene, $A^2$ is lower alkylene, a direct bond or the group —CO—, $Q^1$ is an oxygen atom or the group —$NR^2$—, $R^1$ is hydrogen, hydroxy, cyano, nitro, halogen, lower alkoxy, lower alkyl, lower alkoxycarbonyl, phenyl group which is unsubstituted or substituted by halogen, trifluoromethyl, lower alkyl, lower alkoxy, nitro, amino or mono- or di(lower alkyl)amino, a group of the formula —$NR^3R^4$ or a 5-membered saturated, partially unsaturated or aromatic heterocycle which is attached via a carbon atom and contains as the hetero ring member(s) an oxygen or sulfur atom or an imino or lower alkylimino group and optionally one or two nitrogen atoms, and which is unsubstituted or substituted by one or two lower alkyl groups or substituted by a ($C_{3-6}$)-cycloalkyl, hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or alkylenedioxy group, $R^2$ is hydrogen, lower alkyl, or phenyl group which is unsubstituted or substituted by halogen, trifluoromethyl, lower alkyl, lower alkoxy, nitro, amino or mono- or di(lower alkyl)amino, $R^3$ and $R^4$ each is hydrogen, lower alkyl, lower alkoxyalkyl, lower dialkoxyalkyl, lower alkylenedioxyalkyl, lower cyanoalkyl, lower haloalkyl, lower hydroxyalkyl, lower dihydroxyalkyl, lower alkanoyl, lower alkoxycarbonyl or a ($C_{3-7}$)-cycloalkyl group which is unsubstituted or substituted by hydroxy, lower alkoxy, lower alkanoyloxy, lower hydroxyalkyl, lower alkoxyalkyl, lower alkanoyloxyalkyl, oxo, carbamoyl, mono- or di(lower alkyl)carbamoyl or by lower alkylenedioxy or $R^3$ and $R^4$ together with the nitrogen atom are a saturated N-heterocycle selected from 4, 4-($C_{1-4}$alkylenedioxy)-1-pioeridinyl, or selected from the group consisting of unsubstituted 1-azetidinyl, 1-pyrrolidinyl, 1-piperidinyl, 4-morpholinyl, 4-thiomorpholinyl or 4-R5-1-piperazinyl or substituted by one or two lower alkyl groups or one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or lower groups, and $R^5$ is hydrogen, lower alkyl, lower hydroxyalkyl, lower alkoxyalkyl, lower alkanoyloxyalkyl, lower alkanoyl, lower alkoxycarbonyl, carbamoyl, or mono- or di(lower alkyl)carbamoyl, with the privision that n is the integer 0 when q is the integer 1 and $A^2$ is the group —CO—, that $R^1$ is other than cyano, nitro, halogen or lower alkoxycarbonyl, when q is the integer 0 and n is the integer 1 or when q is the integer 1 and $A^2$ is the group —CO—, that $R^1$ is other than hydroxy, cyano, nitro, halogen, lower alkoxycarbonyl, lower alkoxy and —$NR^3R^4$ when q is the integer 1 and $A^2$ is a direct bond, or a pharmaceutically acceptable acid addition salt of a compound of formula I which has one or more basic substituents, and an inert carrier.

27. A pharmaceutical composition according to claim 26, wherein Rd is other than acetyl when Ra is phenyl, Rb and Rc together are the group —CH=CH—CH=CH— and the dotted line is an additional bond.

28. A pharmaceutical composition according to claim 27, wherein Ra is phenyl.

29. A pharmaceutical composition according to claim 28, wherein Rb and Rc together with the carbon atom denoted by α are a group of the formula >$C_α$—CH=CH—CH=CH— which is unsubstituted or substituted by halogen and the dotted line is an additional bond.

30. A pharmaceutical composition according to claim 29, wherein Rb and Rc together with the carbon atom denoted by α is the group of the formula >$C_α$—CH=CCl—CH=CH—.

31. A pharmaceutical composition according to claim 30, wherein $Q^1$ is an oxygen atom, $A^2$ is the group —CO—, $R^1$ is the group —$NR^3R^4$, $R^3$ is lower alkyl or lower alkoxyalkyl and $R^4$ is hydrogen or lower alkyl or $R^3$ and $R^4$ together with the nitrogen atom are a saturated N-heterocycle selected from the group consisting of unsubstituted 1-azetidinyl, 1-pyrrolidinyl, 1-piperidinyl or 4-morpholinyl or substituted by one or two lower alkyl groups or a hydroxy, lower alkoxy, lower hydroxyalkyl or lower alkoxyalkyl group and either m and q are the integer 0 and n is the integer 1 or m and q are the integer 1 and n is the integer 0.

32. A pharmaceutical composition according to claim 31, wherein $A^1$ is methylene and $R^3$ is lower alkyl or lower alkoxyalkyl and $R^4$ is hydrogen or lower alkyl or $R^3$ and $R^4$ together with the nitrogen atom are a 1-azetidinyl, 1-pyrrolidinyl, 1-piperidinyl or 4-morpholinyl group which is unsubstituted or substituted by one or two lower alkyl groups or by a hydroxy, lower alkoxy, lower hydroxyalkyl or lower alkoxyalkyl group.

33. A pharmaceutical composition according to claim 32, wherein $R^3$ is lower alkyl or 2-(lower alkoxy)ethyl and $R^4$ is hydrogen or lower alkyl or $R^3$ and $R^4$ together with the nitrogen atom are 3-(lower alkoxy)-1-azetidinyl, 3-(lower alkoxy)-1-pyrrolidinyl, 2-(lower alkoxyalkyl)-1-pyrrolidinyl, 2-(lower hydroxyalkyl)-1-pyrrolidinyl, 4-hydroxy-1-piperidinyl, 4-(lower alkoxy)-1-piperidinyl, 4-morpholinyl or 2,6-di(lower alkyl)-4-morpholinyl.

34. A pharmaceutical composition according to claim 33, wherein m and q are the integer 0 and n is the integer 1.

35. A pharmaceutical composition according to claim 26, wherein the compound is N,N-dimethyl-10-chloro-4-oxo-3-phenyl-4H-pyrido[2,1-a]-phthalazine-1-carboxamide.

36. A pharmaceutical composition according to claim 26, wherein the compound is N,N-diethyl-10-chloro-4-oxo-3-phenyl4H-pyrido[2,1-a]-phthalazine-carboxamide.

37. A method of treating or preventing muscle tension, stress, insomnia, anxiety or convulsions which comprises administering to a host requiring such treatment an effective amount of a compound of the formula

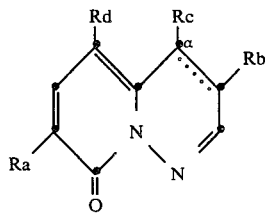

wherein Ra is from the group consisting of unsubstituted phenyl, pyridyl or thienyl or said group substituted by halogen, trifluoromethyl, nitro, lower alkyl or lower alkoxy, Rb and Rc together with the carbon atom denoted by α are a group of the formula >$C_α$—CH=CH—CH=CH— (c) which is unsubstituted or substituted by halogen, trifluoromethyl, lower alkyl, lower alkoxy, nitro, amino or mono- or di(lower alkyl)amino and the dotted line is an additional bond, Rd is the group of the formula —$(A^1)_m$—$(CO)_n$— $(Q^1A^2)_q$—$R^1$, m, n and q each are the integer 0 or 1, $A^1$ is lower alkylene, $A^2$ is lower alkylene, a direct bond or the group —CO—, $Q^1$ is an oxygen atom or the group —$NR^2$—, $R^1$ is hydrogen, hydroxy, cyano, nitro, halogen, lower alkoxy, lower alkyl, lower alkoxycarbonyl, phenyl group which is unsubstituted or substituted by halogen, trifluoromethyl, lower alkyl, lower alkoxy, nitro, amino or mono- or di(lower alkyl)amino, a group of the formula —$NR^3R^4$ or a 5-membered saturated, partially unsaturated or aromatic heterocycle which is attached via a carbon atom and contains as the hetero ring member(s) an oxygen or sulfur atom or an imino or lower alkylimino group and optionally one or two nitrogen atoms, and which is unsubstituted or substituted by one or two lower alkyl groups or substituted by a ($C_{3-6}$)-cycloalkyl, hydroxy, lower alkoxy, lower alkanoyloxy, lower hydroxyalkyl, lower alkoxyalkyl, lower alkanoyloxyalkyl, lower alkoxycarbonyl, lower-alkanoyl, carbamoyl, mono- or di(lower alkyl)carbamoyl, oxo or alkylenedioxy group, $R^2$ is hydrogen, lower alkyl, or phenyl group which is unsubstituted or substituted by halogen, trifluoromethyl, lower alkyl, lower alkoxy, nitro, amino or mono- or di(lower alkyl)amino, $R^3$ and $R^4$ each is hydrogen, lower alkyl, lower alkoxyalkyl, lower dialkoxyalkyl, lower alkylenedioxyalkyl, lower cyanoalkyl, lower haloalkyl, lower hydroxyalkyl, lower dihydroxyalkyl, lower alkanoyl, lower alkoxycarbonyl or a ($C_{3-7}$)-cycloalkyl group which is unsubstituted or substituted by hydroxy, lower alkoxy, lower alkanoyloxy, lower hydroxyalkyl, lower alkoxyalkyl, lower alkanoyloxyalkyl, oxo, carbamoyl, mono- or di(lower alkyl)carbamoyl or by lower alkylenedioxy or $R^3$ and $R^4$ together with the nitrogen atom are a saturated N-heterocycle selected from 4,4-($C_{1-4}$ alkylenedioxy)-piperidinyl, or selected from the group consisting of unsubstituted 1-azetidinyl, 1-pyrrolidinyl, 1-piperidinyl, 4-morpholinyl, 4-thiomorpholinyl or 4-R5-1-piperazinyl or substituted by one or two lower alkyl groups or one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or lower groups, and $R^5$ is hydrogen, lower alkyl, lower hydroxyalkyl, lower alkoxyalkyl, lower alkanoyloxyalkyl, lower alkanoyl, lower alkoxycarbonyl, carbamoyl, or mono- or di(lower alkyl)carbamoyl, with the provision that n is the integer 0 when q is the integer 1 and $A^2$ is the group —CO—, that $R^1$ is other than cyano, nitro, halogen or lower alkoxycarbonyl, when q is the integer 0 and n is the integer 1 or when q is the integer 1 and $A^2$ is the group —CO—, that $R^1$ is other than hydroxy, cyano, nitro, halogen, lower alkoxycarbonyl, lower alkoxy and —$NR^3R^4$ when q is the integer 1 and $A^2$ is a direct bond, or a pharmaceutically acceptable acid addition salt of compound of formula I which has one or more basic substituents.

38. A method according to claim 37, wherein Rd is other than acetyl when Ra is phenyl, Rb and Rc together are the group —CH=CH—CH=CH— and the dotted line is an additional bond.

39. A method according to claim 38, wherein Ra is phenyl.

40. A method according to claim 39, wherein Rb and Rc together with the carbon atom denoted by α are a group of the formula >$C_\alpha$—CH=CH—CH=CH— which is unsubstituted or substituted by halogen and the dotted line is an additional bond.

41. A method according to claim 40, wherein Rb and Rc together with the carbon atom denoted by α is the group of the formula >$C_\alpha$—CH=CCl—CH=CH—.

42. A method according to claim 41, wherein $Q^1$ is an oxygen atom, $A^2$ is the group —CO—, $R^1$ is the group —$NR^3R^4$, $R^3$ is lower alkyl or lower alkoxyalkyl and $R^4$ is hydrogen or lower alkyl or $R^3$ and $R^4$ together with the nitrogen atom are a saturated N-heterocycle selected from the group consisting of unsubstituted 1-azetidinyl, 1-pyrrolidinyl, 1-piperidinyl or 4-morpholinyl or substituted by one or two lower alkyl groups or a hydroxy, lower alkoxy, lower hydroxyalkyl or lower alkoxyalkyl group and either m and q are the integer 0 and n is the integer 1 or m and q are the integer 1 and n is the integer 0.

43. A method according to claim 42, wherein $A^1$ is methylene and $R^3$ is lower alkyl or lower alkoxyalkyl and $R^4$ is hydrogen or lower alkyl or $R^3$ and $R^4$ together with the nitrogen atom are a 1-azetidinyl, 1-pyrrolidinyl, 1-piperidinyl or 4-morpholinyl group which is unsubstituted or substituted by one or two lower alkyl groups or by a hydroxy, lower alkoxy, lower hydroxyalkyl or lower alkoxyalkyl group.

44. A method according to claim 43, wherein $R^3$ is lower alkyl or 2-(lower alkoxy)ethyl and $R^4$ is hydrogen or lower alkyl or $R^3$ and $R^4$ together with the nitrogen atom are 3-(lower alkoxy)-1-azetidinyl, 3-(lower alkoxy)-1-pyrrolidinyl, 2-(lower alkoxyalkyl)-1-pyrrolidinyl, 2-(lower hydroxyalkyl)-1-pyrrolidinyl, 4-hydroxy-1-piperidinyl, 4-(lower alkoxy)-1-piperidinyl, 4-morpholinyl or 2,6-di(lower alkyl)-4-morpholinyl.

45. A method according to claim 44, wherein m and q are the integer 0 and n is the integer 1.

46. A method according to claim 37, wherein the compound is N,N-dimethyl-10-chloro-4-oxo-3-phenyl-4H-pyrido[2,1-a]-phthalazine-1-carboxamide.

47. A method according to claim 37, wherein the compound is N,N-diethyl-10-chloro-4-oxo-3-phenyl-4H-pyrido[2,1-a]-phthalazine-1-carboxamide.

48. A method according to claim 1, methyl 4-oxo-3-phenyl-4H-pyrido[2,1-a]-phthalazine-1-carboxylate, or methyl 10-chloro-4-oxo-3-phenyl-4H-pyrido[2,1-a]-phthalazine-1-carboxylate.

49. A compound according to claim 1, 4-oxo-3-phenyl-4H-pyrido[2,1-a]phthalazine-1-carboxylic acid, or 10-chloro-4-oxo-3-phenyl-4H-pyrido[2,1-a]-phthalazin-1-carboxylic acid.

50. A compound according to claim 1, 3-hydroxy-1-[(4-oxo-3-phenyl-4H-pyrido[2,1-a]-phthalazin-1-yl)carbonyl]azetidine, or (R)-1-[(10-chloro-4-oxo-3-phenyl-4H-pyrido[2,1-a]-phthalazin-1-yl)carbonyl]-2-pyrrolidinemethanol.

* * * * *

UNITED STATES PATENT AND TRADEMARK OFFICE
CERTIFICATE OF CORRECTION

PATENT NO. : 4,855,297

DATED : August 8, 1989

INVENTOR(S) : Ulf Fischer, Fernand Schneider and Widmer Ulrich

It is certified that error appears in the above-identified patent and that said Letters Patent is hereby corrected as shown below:

Column 27, claim 25, line 46, "formula or" should be

-- formula (b) or --

Signed and Sealed this

Seventh Day of January, 1992

Attest:

HARRY F. MANBECK, JR.

*Attesting Officer*      *Commissioner of Patents and Trademarks*